US012661344B2

(12) United States Patent
Wu et al.

(10) Patent No.: US 12,661,344 B2
(45) Date of Patent: Jun. 23, 2026

(54) SAFE AND STABLE NIMODIPINE FORMULATION FOR INJECTION AND METHOD FOR PREPARING SAME

(71) Applicants: SHANGHAI WEI ER BIOPHARMACEUTICAL TECHNOLOGY CO., LTD., Shanghai (CN); SHANGHAI BAOLONG PHARMACEUTICAL CO., LTD., Shanghai (CN); BAOLONG PHARMACEUTICAL CO., LTD., Bozhou (CN); SHANGHAI BAOLONG ANQING PHARMACEUTICAL CO., LTD., Anqing (CN)

(72) Inventors: Xin Wu, Shanghai (CN); Youfa Xu, Shanghai (CN); Zhizhe Lin, Shanghai (CN); Yongjie Huang, Shanghai (CN); Jianming Chen, Shanghai (CN); Yuansheng Zhang, Shanghai (CN); Zhiqin Fu, Shanghai (CN); Xinmei Chen, Shanghai (CN); Hang Chen, Shanghai (CN)

(73) Assignees: SHANGHAI WEI ER BIOPHARMACEUTICAL TECHNOLOGY CO., LTD., Shanghai (CN); SHANGHAI BAOLONG PHARMACEUTICAL CO., LTD., Shanghai (CN); BAOLONG PHARMACEUTICAL CO., LTD., Bozhou (CN); SHANGHAI BAOLONG ANQING PHARMACEUTICAL CO., LTD., Anqing (CN)

( * ) Notice: Subject to any disclaimer, the term of this patent is extended or adjusted under 35 U.S.C. 154(b) by 0 days.

(21) Appl. No.: 18/852,508

(22) PCT Filed: Apr. 4, 2023

(86) PCT No.: PCT/CN2023/086085

§ 371 (c)(1),
(2) Date: Sep. 30, 2024

(87) PCT Pub. No.: WO2023/193694

PCT Pub. Date: Oct. 12, 2023

(65) Prior Publication Data

US 2025/0255854 A1 Aug. 14, 2025

(30) Foreign Application Priority Data

Apr. 6, 2022 (CN) ........................ 202210353082.2

(51) Int. Cl.

| | |
|---|---|
| ***A61K 31/4422*** | (2006.01) |
| ***A61K 9/00*** | (2006.01) |
| ***A61K 9/08*** | (2006.01) |
| ***A61K 47/10*** | (2017.01) |
| ***A61K 47/40*** | (2006.01) |

(52) U.S. Cl.

CPC ........ *A61K 31/4422* (2013.01); *A61K 9/0019* (2013.01); *A61K 9/08* (2013.01); *A61K 47/10* (2013.01); *A61K 47/40* (2013.01)

(58) Field of Classification Search

None

See application file for complete search history.

(56) References Cited

U.S. PATENT DOCUMENTS

| | | | |
|---|---|---|---|
| 2005/0215520 | A1 | 9/2005 | Liu et al. |
| 2007/0244166 | A1 | 10/2007 | Gupta et al. |

FOREIGN PATENT DOCUMENTS

| | | | |
|---|---|---|---|
| CN | 1424035 | A | 6/2003 |
| CN | 1554340 | A | 12/2004 |
| CN | 1634050 | A | 7/2005 |
| CN | 1653089 | A | 8/2005 |
| CN | 1771950 | A | 5/2006 |
| CN | 101129366 | A | 2/2008 |
| CN | 101199522 | A | 6/2008 |
| CN | 102525917 | A | 7/2012 |
| CN | 102552156 | A | 7/2012 |
| CN | 103315948 | A | 9/2013 |
| CN | 105434355 | A | 3/2016 |
| CN | 107019682 | A | 8/2017 |
| CN | 113694031 | A | 11/2021 |

OTHER PUBLICATIONS

Homsek et al. Characterization of nomodipine/beta-cyclodextrin inclusion complex, J. Pharm. Pharmacol. 1998, 50: 180 (Year: 1998).*

Doaa Nabin Maria et al., Nimodipine Opthalmic Formulations for Management of Glaucoma, Pharm Res, vol. 34, Feb. 2, 2017, pp. 809-824 (Year: 2017).*

Jun. 18, 2023 International Search Report issued in International Patent Application No. PCT/CN2023/086085.

(Continued)

*Primary Examiner* — Adam C Milligan
*Assistant Examiner* — Jed A Kucharczk

(57) ABSTRACT

The present invention relates to the technical field of pharmaceutics, and in particular, to a safe and stable nimodipine formulation for injection and a method for preparing same. The present invention provides a lyophilized nimodipine-cyclodextrin powder for injection, comprising sulfobutylether-β-cyclodextrin, which can significantly improve the solubility, safety, and dilution stability of nimodipine, and increase patient compliance and the convenience of clinical use. Compared with a commercially available nimodipine injection NIMOTOP, the present invention has significant advantages in safety and dilution stability.

12 Claims, 6 Drawing Sheets

(56) References Cited

OTHER PUBLICATIONS

Jun. 18, 2023 Written Opinion of the International Searching Authority issued in International Patent Application No. PCT/CN2023/086085.
Doaa Nabin Maria et al., Nimodipine Ophthalmic Formulations for Management of Glaucoma, Pharm Res, vol. 34, Feb. 2, 2017, pp. 809-824.
Wang, Hui et al., Biological Effect of Noveal Cyclodextrin Derivative HPn-SBEm-β-CD Intravenous Administration on Animals, Journal of Southeast University (Medical Science Edition), vol. 30, No. 2, Apr. 30, 2011, pp. 283-290.
Yang, Xinghao et al., The Characteristics of Nimodipine/SBE7-β-CD Inclusion Complex, Chinese Journal of Modern Applied Pharmacy, vol. 20, No. 5, Oct. 31, 2003, pp. 380-383.
Novac, M. et al., Manufacturing and Assessing the New Orally Disintegrating Tablets, Containing Nimodipine-hydroxypropyl-β-cyclodextrin and Nimodipine-methyl-β-cyclodextrin Inclusion Complexes, molecules, vol. 27, Mar. 21, 2022, pp. 1-24.
Farouk Semcheddine et al., Effects of the Preparation Method on the Formation of True Nimodipine SBE-β-CD/HP-β-CD Inclusion Complexes and Their Dissolution Rates Enhancement, AAPS PharmDciTech, vol. 16, No. 3, Jun. 30, 2015, pp. 704-715.
A. P. Carlson et al., Nimodipine Reappraised: An Old Drug With a Future, Curr Neuropharmacol, 2020, 18(1): 65-82.
Z. Teng et al., Preparation and characterization of nimodipine-loaded nanostructured lipid systems for enhanced solubility and bioavailability, Int J Nanomedicine, 2018, 14: 119-133.
Schneider ACR et al., Chronic exposure to ethanol causes steatosis and inflammation in zebrafish liver, World J Hepatol, 2017, 9(8): 418-426.
Xuefen Wu et al., Interaction between β-cyclodextrin and dihydropyridines (Study on inclusion interaction of β-CD with 1,4-dihydropyridine derivates), Chinese Journal of Pharmacy, 2005 (08): 599-601.
S. Tongiani et al., Sulfobutyl ether-alkyl ether mixed cyclodextrin derivatives with enhanced inclusion ability. J Pharm Sci. 2009, 98(12): 4769-4780.

* cited by examiner

SAFE AND STABLE NIMODIPINE FORMULATION FOR INJECTION AND METHOD FOR PREPARING SAME

The present application is a National Stage of International Application No. PCT/CN2023/086085, filed on Apr. 4, 2023, which claims priority of the Chinese Patent Application No. CN202210353082.2 filed on Apr. 6, 2022.

TECHNICAL FIELD

The present disclosure is related to the field of pharmaceutical technology, specifically, safe and stable nimodipine for injection and its preparation method.

BACKGROUND

Nimodipine (the structural formula shown in formula I) is a yellow crystalline powder with a melting point of 125° C.; it is almost insoluble in water, soluble in ethanol and chloroform, and very easy to degrade when exposed to light. Nimodipine easily crosses the blood-brain barrier, acts on the smooth muscle of cerebral blood vessels, dilates cerebral blood vessels, increases cerebral blood flow, and can effectively prevent or reverse ischemic damage to brain tissue caused by cerebral vasospasm due to subarachnoid hemorrhage. It is clinically used for the prevention and treatment of ischemic cerebrovascular diseases, such as ischemic nerve injury caused by cerebral vasospasm after subarachnoid hemorrhage, migraine, sudden deafness, etc., and has great potential in the treatment of cerebrovascular diseases. (Carlson A P, et al. Nimodipine Reappraised: An Old Drug with a Future. Curr Neuropharmacol. 2020; 18 (1): 65-82).

Structural formula I

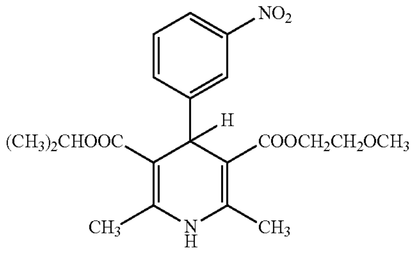

Nimodipine is currently available as a tablet, capsule, oral solution, or injection. After oral administration of nimodipine, the hepatic first-pass effect is significant, and the bioavailability is only 5-15%. Additionally, the half-life of nimodipine is short, and patients need to be given the drug frequently to maintain an effective blood concentration, which greatly limits oral drug administration. (Teng Z, et al. Preparation and characterization of nimodipine-loaded nanostructured lipid systems for enhanced solubility and bioavailability. International Journal of Nanomedicine. 2018; 14:119-133.)

To improve the shortcomings of the oral formulation of nimodipine, Bayer of Germany has developed a nimodipine injection. With no hepatic first-pass effect, high bioavailability, and rapid onset of action, nimodipine for injection has unparalleled advantages over other dosage forms in clinical use. However, this injection has the following problems: (i) Due to the poor solubility of nimodipine in water, many organic solvents, including 23.7% (V/V) ethanol and 17% (V/V) polyethylene glycol 400, were added to the nimodipine injection mixture to increase the solubility of nimodipine. Large amounts of organic solvents are highly irritating to blood vessels, causing pain, redness, and swelling at the site of administration, which can easily lead to phlebitis, resulting in poor patient compliance. (Schneider A C, et al. Chronic exposure to ethanol causes steatosis and inflammation in zebrafish liver. World J Hepatol. 2017; 9 (8): 418-426.) (ii) Nembutal injection results in easy precipitation when the drug is directly diluted for clinical use. Therefore, it needs to be mixed with 5% dextrose, 0.9% sodium chloride, and other liquids at a ratio of 1:4 (v/v) with the help of a three-way valve; the daily administration time is 10 h, and the treatment time is 10-14 days. This infusion method has major safety risks, the drip speed and mixing ratio are not easy to control, the operation is cumbersome and long, which is very inconvenient for clinical use, and patient compliance is poor.

Given the shortcomings of the existing formulations of nimodipine, researchers in the industry have carried out extensive studies on nimodipine.

To improve the solubility of nimodipine, researchers have used nanomanufacturing technologies such as fat emulsions, liposomes, and lipid nanoparticles to encapsulate nimodipine, such as the Chinese patent documents CN107019682A, CN102552156A, CN101199522A, CN1554340A, and CN105434355A. Although the water solubility of nimodipine has improved, nanoformulations have problems such as easy aggregation of particles, low drug loading, a low encapsulation rate, and obvious sudden release effects, and they are easily captured by the hepatic and splenic reticuloendothelial systems, which affects therapeutic efficacy and even increases toxicity. In addition, the preparation process of nanoformulations is complicated, the production line requirements are high, the cost is high, and the product quality is difficult to control.

Other researchers have used surfactants and polymers to form micelles with nimodipine, thus increasing its water solubility. For example, the Chinese patent documents CN101129366A and CN1771950A, in which surfactants with great toxicity, such as Tween 80, are used in the formula, easily lead to hemolysis and allergic reactions and are highly irritable, the Chinese patent documents CN113694031A, CN102525917A, and CN103315948A use polymers to encapsulate nimodipine, but the in vivo process of polymer micelles is unpredictable, which affects therapeutic efficacy.

Given the above shortcomings of nanoformulations, researchers have begun to look for new formulation techniques to improve the water solubility of nimodipine, among which nimodipine cyclodextrin inclusion is one of the current research hotspots, and many domestic and foreign scholars have carried out many studies.

It has been reported in the literature that nimodipine is difficult to encapsulate with β-cyclodextrin because of the high spatial resistance of the side chain. (Wu Xuefen, et al. Interaction between β-cyclodextrin and dihydropyridines[J]. Chinese Journal of Pharmacy, 2005 (08): 599-601). Given the inadequacy of β-cyclodextrin, researchers have attempted to find new β-cyclodextrin derivatives that encapsulate nimodipine.

The Chinese patent document CN1634050A discloses a new nimodipine composition for injection, the composition comprising nimodipine, polyethylene glycol 400, Tween 80, and hydroxypropyl-β-cyclodextrin. There are several obvious defects in this technology: (i) In addition to hydroxypropyl-β-cyclodextrin, a large amount of Tween 80 and polyethylene glycol 400 are added to aid solubility in the formula, and the prescription process is complicated. (ii) Lyophilized products add polyethylene glycol 400, leading to the appearance of product shrinkage, collapse, and failure; (iii) the formula contains Tween 80, which easily leads to hemolysis, allergic reactions, and strong irritation.

The Chinese patent document CN1424035A discloses a nimodipine lyophilized composition, the composition comprising a phospholipid, a cyclodextrin and a derivative thereof or a surfactant, where the mass ratio of nimodipine to cyclodextrin and a derivative thereof ranges from 1:1 to 1:20. The Chinese patent document CN1653089A discloses an organic drug and β-cyclodextrin derivative complex and its preparation method, in which the mass ratio of nimodipine/hydroxypropyl-β-cyclodextrin is 1:136.

The above patents generally have the following problems: (i) The relative proportions of hydroxypropyl-β-cyclodextrin and the drug are too high, and the coating effect is poor. (ii) A large number of organic solvents are added to the formula to aid solubility, which is highly irritating. (iii) The existence of many organic solvents is not conducive to cyclodextrin encapsulation. In summary, solving the above technical defects of cyclodextrin inclusion complexes is still a hot topic in current research. In recent years, injections containing sulfobutyl ether-β-cyclodextrin have been marketed, and the application of sulfobutyl ether-β-cyclodextrin in pharmaceutical preparations has attracted extensive attention from researchers. Sulfobutyl-β-cyclodextrin reportedly has a significantly better solubilizing effect on nimodipine than does hydroxypropyl-β-cyclodextrin. Sulfobutyl-β-cyclodextrin is a more ideal carrier for nimodipine than hydroxypropyl-β-cyclodextrin. (Semcheddine F, et al. Effects of the Preparation Method on the Formation of True Nimodipine SBE-β-CD/HP-β-CD Inclusion Complexes and Their Dissolution Rates Enhancement. AAPS PharmSciTech. 2015; 16 (3): 704-715).

A literature search revealed that some scholars have used the grinding method to prepare nimodipine sulfobutyl ether-β-cyclodextrin inclusion complexes. The inclusion complexes prepared by this method have low drug loading and need to be filtered under suction and washed to remove the undissolved drug after the completion of the preparation, the reproducibility is poor, the product quality is difficult to guarantee, and it is not suitable for industrial production (Yang Xinghao, Ren Yong. Characterization of nimodipine/sulfobutyl ether-β-cyclodextrin solid inclusion complexes [J]. China Modern Applied Pharmacy, 2003 (05): 380-383). Many researchers have used shaking methods to prepare nimodipine sulfobutyl ether-β-cyclodextrin inclusion complexes. Serena et al. prepared nimodipine sulfobutyl ether-β-cyclodextrin inclusion complexes by mixing an excess of nimodipine into a 50 mM aqueous solution of sulfobutyl ether-β-cyclodextrin and shaking it for 48 h on a shaker at room temperature. (Tongiani S, et al. Sulfobutyl ether-alkyl ether mixed cyclodextrin derivatives with enhanced inclusion ability. J Pharm Sci. 2009; 98 (12): 4769-4780); Farouk et al. prepared a nimodipine sulfobutyl ether-β-cyclodextrin inclusion complex by adding excess nimodipine to a 16 mM aqueous solution of sulfobutyl ether-β-cyclodextrin and mixing and shaking on a shaker for 72 h at 37° C. (Semcheddine F, et al. Effects of the Preparation Method on the Formation of True Nimodipine SBE-β-CD/HP-β-CD. Inclusion Complexes and Their Dissolution Rate Enhancement. AAPS Pharm Sci Tech. 2015; 16 (3): 704-715); Doaa Nabih et al. prepared a nimodipine sulfobutyl ether-β-cyclodextrin inclusion complex by adding excess nimodipine to aqueous sulfobutyl ether-β-cyclodextrin solution and mixing, and the resulting suspension was vortexed for 5 min, ultrasonicated for 15 min, and finally shaken on a shaker at 37° C. for 72 h. (Maria D N, et al. Nimodipine Ophthalmic Formulations for Management of Glaucoma. Pharm Res. 2017; 34 (4): 809-824). The above studies all used the shaking method to prepare inclusion complexes, and the cyclodextrin inclusion complexes prepared by this method had poor inclusion effects. In addition, because of the lack of systematic studies on the amount of sulfobutyl ether-β-cyclodextrin, inclusion temperature, inclusion time, ethanol dosage, sulfobutyl ether-β-cyclodextrin and nimodipine mass ratio (excipient ratio), and stirring speed in those studies. This led to the common problems of long preparation times, low solubility of nimodipine, and high excipient ratios.

In summary, the existing technologies generally have poor cyclodextrin encapsulation effects, long preparation times, and high excipient ratios, the formulations need to add a large number of organic solvents to aid solubility in addition to cyclodextrins, which are not conducive to cyclodextrin encapsulation and, at the same time, increase the irritation and toxicity of the formulation and have low safety. Therefore, developing a safe and stable nimodipine injection, which can lay a solid foundation for improving the safety and convenience of nimodipine clinical use, is highly important.

CONTENT OF THE PRESENT INVENTION

Given that the above methods do not fundamentally address the defects of poor dilution stability and low safety of nimodipine injection, the present disclosure aims to provide safe and stable nimodipine for injection and preparation methods.

The present technique increases the solubility of nimodipine via the addition of sulfobutyl ether-β-cyclodextrin. Preliminary literature research and experimental verification revealed that sulfobutyl ether-β-cyclodextrin is a more ideal carrier for nimodipine; however, few studies have investigated nimodipine sulfobutyl ether-β-cyclodextrin inclusion compounds, and a nimodipine sulfobutyl ether-β-cyclodextrin inclusion compound product that is suitable for industrial production and can be applied in the clinic has not yet been developed.

The inventor prepared nimodipine lyophilized powder injection according to the Chinese patent document CN1634050A. The formulation contains Tween 80, which easily causes hemolysis and allergic reactions and is highly irritable. Moreover, the lyophilized powder injection obtained from the preparation is loose in space and collapsed (see Example 1), and the appearance of the unqualified lyophilized powder injection affects the product quality.

The inventor prepared a 2-hydroxypropyl-β-cyclodextrin-containing nimodipine powder injection according to Example 2 in the Chinese patent document CN1424035A. Multiple experiments revealed that the drug precipitated during preparation, and even when the nimodipine cyclodextrin inclusion complex was prepared at the maximum excipient percentage in the patent (drug/2-hydroxypropyl-β-cyclodextrin mass ratio of 1:20), the drug could not be completely encapsulated, and the actual excipient ratio was measured to be 571 (see Example 2).

The inventor operated according to Example 28 in the Chinese patent document CN1653089A, and after many experiments, the drug was precipitated during the preparation process. The actual measured excipient ratio was 1904 (see Example 3), which was much higher than the excipient ratio of the present disclosure.

The inventors also adopted the shaking method used in the literature for the preparation of nimodipine sulfobutyl ether-β-cyclodextrin inclusion complexes, shaking at 37° C. for 72 h, with the addition of an appropriate amount of ethanol to aid solubilization to the formulation, which resulted in the preparation of nimodipine sulfobutyl ether-β-cyclodextrin inclusion complexes with poor encapsulation and a long preparation time, which is not conducive to the industrial production of injectable dosage forms (see Example 4).

Through extensive experimental studies, the amount of sulfobutyl ether-β-cyclodextrin, the encapsulation temperature, the encapsulation time, the amount of ethanol, the excipient ratio, and the stirring speed significantly affect the encapsulation effect of sulfobutyl ether-β-cyclodextrin on nimodipine. The present disclosure can significantly reduce the excipient ratio by adjusting the amount of sulfobutyl ether-β-cyclodextrin, the encapsulation temperature, the encapsulation time, the amount of ethanol, and the stirring speed to achieve a desirable drug loading concentration, and the safety and dilution stability of the formulation are good. In addition, the formulations of the present disclosure may contain a small amount of ethanol, and dissolving nimodipine in a small amount of ethanol improves the solubility of the drug in an aqueous solution of sulfobutyl ether-β-cyclodextrin, increases the ease of the preparation process, and the ethanol can be removed during the preparation process, leaving less residue in the product (see Examples 33 and 65).

In the first aspect of the present disclosure, a safe and stable nimodipine for injection, made from sulfobutyl ether-β-cyclodextrin and nimodipine, is provided at a mass ratio of 200:1-700:1.

Furthermore, the mass ratio of sulfobutyl ether-β-cyclodextrin to nimodipine is 350:1-700:1.

Furthermore, nimodipine for injection contains 0.01-0.14% g/ml nimodipine before lyophilization and 10-50% g/ml sulfobutyl ether-β-cyclodextrin before lyophilization.

Furthermore, sulfobutyl ether-β-cyclodextrin and nimodipine have mass ratios of 400:1-600:1, the nimodipine content ranges from 0.02-0.10% g/ml, and the concentration of sulfobutyl ether-β-cyclodextrin ranges from 10-40% g/ml.

Furthermore, sulfobutyl ether-β-cyclodextrin and nimodipine have mass ratios of 450:1-550:1, the nimodipine content is 0.04-0.06% g/ml, and the concentration of sulfobutyl ether-β-cyclodextrin is 20-30% g/ml.

A safe and stable nimodipine for injection of the present disclosure is made from the following components:

| | |
|---|---|
| nimodipine | 0.01-0.20% g/ml |
| Sulfobutyl ether-β-cyclodextrin | 10-50% g/ml |
| Ethanol | 0-5% ml/ml |
| Water for Injection | tolerance. |

Furthermore, nimodipine for injection is made from the following components:

| | |
|---|---|
| nimodipine | 0.01-0.14% g/ml |
| Sulfobutyl ether-β-cyclodextrin | 10-50% g/ml |
| Ethanol | 0-3.5% ml/ml |
| Water for Injection | tolerance. |

Furthermore, nimodipine for injection is made from the following components:

| | |
|---|---|
| nimodipine | 0.02-0.10% g/ml |
| Sulfobutyl ether-β-cyclodextrin | 10-40% g/ml |
| Ethanol | 0-2.5% ml/ml |
| Water for Injection | tolerance. |

Furthermore, nimodipine for injection is made from the following components:

| | |
|---|---|
| nimodipine | 0.04-0.06% g/ml |
| Sulfobutyl ether-β-cyclodextrin | 20-30% g/ml |
| Ethanol | 0-1.5% ml/ml |
| Water for Injection | tolerance. |

Furthermore, the above-described nimodipine for injection does not contain ethanol.

Furthermore, the above-described nimodipine for injection may also contain a buffer to adjust the pH to 4.5-7.5; this buffer is selected from sodium citrate-citric acid, disodium hydrogen phosphate-citric acid, disodium hydrogen phosphate-sodium dihydrogen phosphate, disodium hydrogen phosphate-potassium dihydrogen phosphate, and potassium dihydrogen phosphate-sodium hydroxide.

A second aspect of the present disclosure is a preparation method for the safe and stable nimodipine for injection as described above, which comprises the following steps:

(a) weighing the prescribed amount of sulfobutyl ether-β-cyclodextrin (and buffer), adding an appropriate amount of water for injection, and stirring at a certain temperature to dissolve to obtain a sulfobutyl ether-β-cyclodextrin aqueous solution;

(b) weighing the prescribed amount of nimodipine and adding the prescribed amount of ethanol to dissolve to obtain a nimodipine ethanol solution;

(c) adding the solution of step (b) or nimodipine powder to the solution of step (a) under a certain stirring temperature and speed, stirring for a certain period, adding water for injection to the full amount, sterilely filtering with a 0.22 μm microporous filter membrane, filling, freeze-drying, and packaging to obtain the safe and stable nimodipine for injection.

Furthermore, the stirring temperature described in steps (a) and (c) is 20-100° C.; furthermore, 40-95° C. is preferable, and 60-90° C. is more preferable.

Furthermore, the stirring time described in step (c) is 10-300 min, preferably 30-240 min, more preferably 60-180 min.

Furthermore, the stirring speed described in step (c) is 0.5-10.0 m/s, preferably 0.8-6.0 m/s, more preferably 1.0-3.0 m/s.

Furthermore, steps (a), (b), and (c) may be saturated with clean, dry nitrogen ($N_2$), including freeze-drying followed by nitrogen charging and encapsulating.

Furthermore, the ethanol residue of nimodipine for injection, as described in step (c), is less than 0.3%, preferably less than 0.1%, and more preferably less than 0.05%.

Through extensive experimental studies, the amount of sulfobutyl ether-β-cyclodextrin, the encapsulation temperature, the encapsulation time, the amount of ethanol, the excipient ratio, and the stirring speed significantly affect the encapsulation effect of sulfobutyl ether-β-cyclodextrin on nimodipine. The control conditions of the present disclosure can significantly reduce the relative ratios of sulfobutyl ether-β-cyclodextrin and nimodipine, improve the safety and dilution stability of the preparation, and overcome the defects of the commercially available Nimotop injection. Therefore, controlling the amount of sulfobutyl ether-β-cyclodextrin, the encapsulation temperature, the encapsulation time, the amount of ethanol, the excipient ratio, and the stirring speed are the core technologies of the present disclosure.

The advantages of this disclosure are as follows:

1. The safety of the nimodipine for injection of the present disclosure has improved significantly to avoid the use of a large number of organic solvents caused by the toxicity of the problem, the irritation of the preparation is reduced, and the use compliance of patients is improved.
2. Improved dilution stability. Nimodipine for injection can be dispersed directly into 0.9% sodium chloride injection or 5% dextrose injection after reconstruction, without the need to use a three-way valve, improving the convenience of use.
3. The relative ratio of sulfobutyl ether-β-cyclodextrin to nimodipine in the nimodipine for injection used in the present disclosure is relatively small, which not only reduces the production cost but also reduces the safety hazards that may be caused by cyclodextrin.
4. Increase the convenience of production. Compared with the commonly used shaking method, this method can greatly shorten the preparation time by optimizing the preparation process; at the same time, the use of a small amount of ethanol not only shortens the encapsulation time, but also the small amount of ethanol in the formulation does not need a special procedure to be removed. The formulation can achieve very low ethanol residue in the end product, which increases the convenience of production and shortens the production cycle.

In summary, the present disclosure provides a nimodipine cyclodextrin lyophilized powder injection containing sulfobutyl ether-β-cyclodextrin, which can significantly improve the solubility of nimodipine, the safety of dosing and the stability of dilution, and increase the compliance of use by patients and the convenience of clinical use. Compared with commercially available Nimotop®, the present disclosure has obvious advantages in terms of significantly reduced toxicity, significantly improved safety, dilution stability, and convenience of clinical use. Compared with the existing technology of the nimodipine cyclodextrin inclusion complex, it avoids the use of many organic solvents, surfactants and so on, greatly reduces the ratio of excipients, shortens the production cycle, and has very good application prospects.

DETAILED DESCRIPTION OF THE PREFERRED EMBODIMENT

Figure 1:
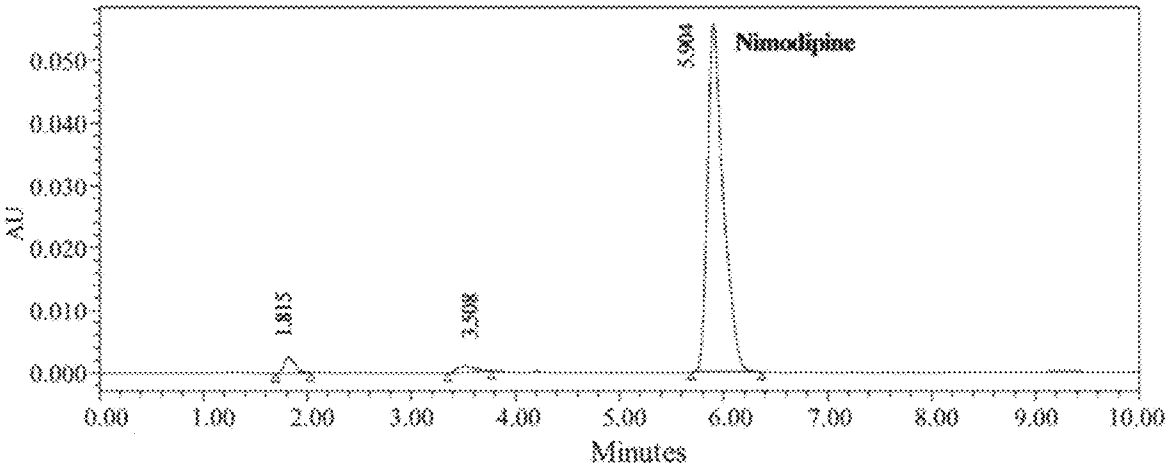
FIG. 1 HPLC chromatogram of the test solution for content determination.

Specific embodiments of the present disclosure are described in detail below in connection with embodiments. The following embodiments are intended only to illustrate the disclosure and not to limit the scope of the disclosure.

Example 1: Effect of Polyethylene Glycol 400 on Nimodipine Freeze-Dried Powder Injection In accordance with the patent literature CN1634050A Example 1, an operation experiment was carried out to prepare nimodipine freeze-dried powder injection.

1. Prescription

| | |
|---|---|
| Nimodipine | 0.1 g |
| Polyethylene glycol 400 | 1 g |
| Tween 80 | 1 g |
| Hydroxypropyl-β-cyclodextrin | 2.5 g |
| Water for injection | 50 mL |

2. Preparation Process

The prescribed amount of nimodipine was added to a mixture of polyethylene glycol 400 and Tween-80, heated and stirred until it dissolved. Hydroxypropyl-β-cyclodextrin was added to the water for injection, heated and stirred to dissolve, and the above mixture was added while stirring and stirred at room temperature. An appropriate amount of activated carbon was added, the mixture was heated at 60° C. for 20 min, and the mixture was stirred Filtration, filling, and freeze-drying were performed.

3. Experimental Results

The freeze-dried powder injection prepared with this formula has loose voids, and the appearance shrinks, collapses and is not full. The appearance of unqualified freeze-dried powder injection affects the quality of the product.

Example 2: Preparation of the Nimodipine Hydroxypropyl-β-Cyclodextrin Inclusion Complex In accordance with the Chinese patent literature CN1424035A Example 2, an operation experiment was carried out to prepare a nimodipine hydroxypropyl-β-cyclodextrin inclusion complex for freeze-dried powder injection.

1. Prescription.

| | |
|---|---|
| Nimodipine | 2 mg |
| Anhydrous ethanol | 2 mL |
| Hydroxypropyl-β-cyclodextrin | 20 mg |
| Water for injection | 7 mL |

2. Preparation process

Two milligrams of nimodipine was taken and added with 2 mL of anhydrous ethanol, and the mixture was stirred until completely dissolved. A total of 20 mg of hydroxypropyl-β-cyclodextrin was taken and dissolved in 7 mL of water for injection. Under stirring, a nimodipine ethanol solution was added to a hydroxypropyl-β-cyclodextrin aqueous solution to make a uniform cyclodextrin inclusion complex. The ethanol was removed by vacuum drying on a rotary evaporator, and 300 mg of mannitol was added. The solution was filtered with a presterilized vertical melting funnel. The filtrate was placed in a sterile vial, and the content was determined by high-performance liquid chromatography. The samples were freeze-dried and sealed to obtain injection of nimodipine powder.

3. The method used to determine the content of nimodipine in this disclosure is high-performance liquid chromatography (2020 edition of the Chinese Pharmacopoeia, General Principle 0512), which is performed in the dark.

Chromatographic conditions and system suitability test: Octadecylsilane-bonded silica gel was used as the filler (C18 column 250×4.6 mm, 5 μm); the mobile phase was methanol-acetonitrile-water (35:38:27). The detection wavelength was 235 nm. The injection volume was 10 μL. The theoretical plate number is not less than 8000 according to the calculation of the nimodipine peak, and the separation degree of the nimodipine peak and adjacent impurity peak should meet the requirements.

To prepare the test solution, 1 mL of the prepared solution was accurately measured, placed in a 50 mL volumetric flask, diluted with the mobile phase to scale, and shaken well. The HPLC chromatogram of the test solution is shown in FIG. 1.

Preparation of the reference solution: The nimodipine reference substance was accurately weighed, dissolved with the mobile phase and quantitatively diluted to make a solution containing approximately 20 μg per 1 mL.

Determination method: The test solution and the reference solution were accurately measured and injected into the liquid chromatograph, and chromatographic diagrams were recorded. The peak area was calculated via the external standard method.

4. Experimental results

During the mixing and stirring process of the nimodipine ethanol solution and hydroxypropyl-β-cyclodextrin aqueous solution, the drug precipitated. After the sample was filtered, the drug content in the solution was determined to be 0.005 mg/mL, and the excipient ratio was calculated to be 571.

5. Result analysis

The use of 22% ethanol in this patented technology is not conducive to the inclusion of nimodipine by cyclodextrin, and a large amount of ethanol has certain safety hazards. In addition, the need to remove ethanol by rotary evaporation increases the complexity of the process.

Example 3: Preparation of the Nimodipine Hydroxypropyl-β-Cyclodextrin Inclusion Complex The operation experiment was carried out according to the Chinese patent document CN1653089A Example 28 to prepare the nimodipine hydroxypropyl-β-cyclodextrin inclusion complex.

1. Prescription

| | |
|---|---|
| Nimodipine | 0.5 g |
| Ethanol | 10 mL |
| Hydroxypropyl-β-cyclodextrin | 68 g |
| Water for injection | 170 mL |

2. Preparation Process

First, 0.5 g of nimodipine was dissolved in the prescribed amount of ethanol, and 68 g of hydroxypropyl-β-cyclodextrin was dissolved in the appropriate amount of water. The above mixture was mixed, stirred and heated at 60° C., activated carbon was added to remove the heat source, the mixture was filtered, and the filtrate was added to a 1 L rotary tank. The temperature was maintained at 70-80° C., the solvent was concentrated under reduced pressure, and the solvent was recovered and converted into a water system. Heat preservation was continued, and the pressure was reduced to expand and dry the material.

3. Experimental Results

After many experiments were verified, the drug was precipitated during the mixing and stirring process of the nimodipine ethanol solution and hydroxypropyl-β-cyclodextrin aqueous solution. In the process of vacuum drying to remove ethanol, the drug is also precipitated in large quantities. After the sample was filtered, the drug content in the solution was determined to be 0.21 mg/mL, and the calculated excipient ratio was 1904, which was much higher than the excipient ratio of the present disclosure.

Example 4: Preparation of a Nimodipine Sulfobutyl Ether-β-Cyclodextrin Inclusion Complex by Shaking In accordance with the literature, a nimodipine sulfobutyl ether-β-cyclodextrin inclusion complex (Maria D N, et al. Nimodipine Ophthalmic Formulations for Management of Glaucoma. Pharm Res. 2017; 34 (4): 809-824.) was prepared via the shaking method. In addition, a nimodipine sulfobutyl ether-β-cyclodextrin inclusion complex was prepared via the shaking method with the same formula containing a small amount of ethanol, and the results were compared.

1. Prescription

TABLE 1

| Prescription design | | |
|---|---|---|
| Components | Prescription 1 | Prescription 2 |
| Nimodipin | 30 mg | 30 mg |
| Ethanol | — | 0.6 mL |
| Sulfobutyl ether-β-cyclodextrin | 1.3 g | 1.3 g |
| Water for injection | Filling up to 30 mL | Filling up to 30 mL |

2. Preparation Process

Sulfobutyl ether-β-cyclodextrin (1.3 g) was respectively taken for two parallel experiments. An appropriate amount of water for injection was added, and the solution was dissolved by stirring to obtain a sulfobutyl ether-β-cyclodextrin aqueous solution. One group did not add ethanol, and the other group added the prescription amount of ethanol to the sulfobutyl ether-β-cyclodextrin aqueous solution for mixing. The two groups were supplemented with water for injection to 30 mL, placed in a vial, added to the prescription amount of nimodipine, plugged and covered, vortexed for 5 min, sonicated for 15 min, and oscillated in an electric thermostatic water bath at 37° C. for 72 h. The obtained solution was filtered through a 0.45 μm polyethersulfone filter membrane, and the content of nimodipine was detected by HPLC.

3. Experimental Results

TABLE 2

Solubility of the nimodipine sulfobutyl ether-β-cyclodextrin inclusion complex prepared by shaking

| Check projects | Prescription 1 | Prescription 2 |
|---|---|---|
| Drug content (mg/mL) | 0.10 | 0.09 |
| Excipient ratio | 456 | 462 |

The results showed that even if a small amount of ethanol was added to the formulation, the inclusion effect of the nimodipine sulfobutyl ether-β-cyclodextrin inclusion complex prepared by shaking for 72 h was poor, and the preparation time was long, which was not conducive to industrial production via injection.

Example 5: Effects of Different Solvents on the Solubility of Nimodipine in Sulfobutyl Ether-β-Cyclodextrin 1. Prescription

TABLE 3

Prescription design

| Components | Prescription 1 | Prescription 2 | Prescription 3 | Prescription 4 | Prescription 5 |
|---|---|---|---|---|---|
| Nimodipine | 45 mg | 45 mg | 45 mg | 45 mg | 45 mg |
| Ethanol | 0.9 mL | | — | — | — |
| Polyethylene glycol 400 | — | 0.9 mL | — | — | — |
| Propylene glycol | — | — | 0.9 mL | — | |
| Acetone | — | — | | 0.9 mL | |
| Sulfobutyl ether-β-cyclodextrin | 9 g | 9 g | 9 g | 9 g | 9 g |
| Water for injection | | | Filling to 30 mL | | |

2. Preparation Process

Sulfobutyl ether-β-cyclodextrin (9 g, parallel 5 groups) was added, an appropriate amount of water for injection was added, and the mixture was stirred at 30° C. to dissolve to obtain a sulfobutyl ether-β-cyclodextrin aqueous solution; 45 mg of nimodipine was dissolved in 0.9 mL of solvent. Under stirring conditions, nimodipine solution was added to sulfobutyl ether-β-cyclodextrin aqueous solution and stirred for 2 h. The obtained solution was filtered through a 0.45 μm polyethersulfone filter membrane, and the content of nimodipine was detected via high-performance liquid chromatography (HPLC).

3. Experimental Results

TABLE 4

Effects of different solvents on the solubility of nimodipine in sulfobutyl ether-β-cyclodextrin

| Check projects | Ethanol | Polyethylene glycol 400 | Propylene glycol | Acetone | Solvent-free |
|---|---|---|---|---|---|
| Drug content (mg/mL) | 0.70 | 0.59 | 0.37 | 0.65 | 0.26 |
| Excipient ratio | 429 | 508 | 811 | 462 | 1154 |

The results showed that the addition of an appropriate amount of organic solvent was beneficial for the solubilization of nimodipine by cyclodextrin, and the best effect was achieved with ethanol.

Example 6: Effect of Ethanol Dosage on the Solubility of Nimodipine in Sulfobutyl Ether-β-Cyclodextrin 1. Prescription

TABLE 5

| Prescription design | | | | | | | |
|---|---|---|---|---|---|---|---|
| | Ethanol volume | | | | | | |
| Components | 1% | 2% | 3% | 4% | 5% | 6% | 10% |
| Nimodipine | 15 mg | 15 mg | 15 mg | 15 mg | 15 mg | 15 mg | 15 mg |
| Ethanol | 0.3 mL | 0.6 mL | 0.9 mL | 1.2 mL | 1.5 mL | 1.8 mL | 3 mL |
| Sulfobutyl ether-β-Cyclodextrin | 6 g | 6 g | 6 g | 6 g | 6 g | 6 g | 6 g |
| Water for injection | Filling to 30 mL | | | | | | |

2. Preparation Process

Sulfobutyl ether-β-cyclodextrin (6 g, parallel 7 groups) was added, an appropriate amount of water for injection was added, and the mixture was stirred at 30° C. to dissolve to obtain a sulfobutyl ether-β-cyclodextrin aqueous solution; 15 mg of nimodipine was dissolved in 0.6 mL, 0.9 mL, 1.2 mL, 1.5 mL or 1.8 mL of ethanol. An ethanol solution of nimodipine was added to an aqueous solution of sulfobutyl ether-β-cyclodextrin under stirring conditions. The solution was stirred for 2 h, and the obtained solution was filtered through a 0.45 μm polyethersulfone filter membrane. The content of nimodipine was detected by HPLC.

3. Experimental Results

The content of the prepared nimodipine cyclodextrin was determined. The results are as follows:

TABLE 6

| Effects of different ethanol dosages on the solubility of nimodipine in sulfobutyl ether-β-cyclodextrin | | | | | | | |
|---|---|---|---|---|---|---|---|
| | Ethanol volume | | | | | | |
| Check projects | 1% | 2% | 3% | 4% | 5% | 6% | 10% |
| Drug content (mg/mL) | 0.28 | 0.22 | 0.20 | 0.19 | 0.18 | 0.16 | 0.14 |
| Excipient ratio | 711 | 914 | 1048 | 1068 | 1121 | 1154 | 1430 |

The experimental results revealed that with increasing ethanol dosage, the solubility of nimodipine in a sulfobutyl ether-β-cyclodextrin aqueous solution decreased, and the excipient ratio increased.

Example 7: Effect of Sulfobutyl Ether-β-Cyclodextrin Dosage on the Solubility of Nimodipine 1. Prescription

TABLE 7

| Prescription design | | | | | | | | |
|---|---|---|---|---|---|---|---|---|
| | Sulfobutyl ether-β-cyclodextrin dosage | | | | | | | |
| Components | 10% | 20% | 25% | 30% | 35% | 40% | 45% | 50% |
| Nimodipine | 45 mg | 45 mg | 45 mg | 45 mg | 45 mg | 45 mg | 45 mg | 45 mg |
| Ethanol | 0.9 mL | 0.9 mL | 0.9 mL | 0.9 mL | 0.9 mL | 0.9 mL | 0.9 mL | 0.9 mL |
| Sulfobutyl ether-β-Cyclodextrin | 3 g | 6 g | 7.5 | 9 g | 10.5 g | 12 g | 13.5 g | 15 g |
| Water for injection | Filling to 30 mL | | | | | | | |

2. Preparation Process

Sulfobutyl ether-β-cyclodextrin (3 g, 6 g, 7.5 g, 9 g, 10.5 g, 12 g, 13.5 g and 15 g) was added, and an appropriate amount of water for injection was added. The solution was stirred at 30° C. to obtain a sulfobutyl ether-β-cyclodextrin aqueous solution; 45 mg of nimodipine was dissolved in 0.9 mL of ethanol. An ethanol solution of nimodipine was added to an aqueous solution of sulfobutyl ether-β-cyclodextrin under stirring conditions, and the mixture was stirred for 2 h. The resulting mixture was filtered through a 0.45 μm polyethersulfone filter membrane, and the content of nimodipine was detected via high-performance liquid chromatography (HPLC).

3. Experimental Results

The content of the prepared nimodipine cyclodextrin was determined. The results are as follows:

TABLE 8

Effects of different sulfobutyl ether-β-cyclodextrin dosages on the solubility of nimodipine

| Check projects | Sulfobutyl ether-β-cyclodextrin dosage 10% | 20% | 25% | 30% | 35% | 40% | 45% | 50% |
|---|---|---|---|---|---|---|---|---|
| Drug content (mg/mL) | 0.10 | 0.22 | 0.34 | 0.68 | 0.93 | 1.05 | 1.24 | 1.25 |
| Excipient ratio | 974 | 925 | 735 | 441 | 376 | 370 | 363 | 400 |

The experimental results revealed that when the amount of sulfobutyl ether-β-cyclodextrin was less than 45%, with increasing amounts of sulfobutyl ether-β-cyclodextrin, the solubility of nimodipine increased, and the excipient ratio decreased significantly. When the amount of sulfobutyl ether-β-cyclodextrin was greater than 45%, the solubility of nimodipine did not increase significantly, and the ratio of excipient increased.

Example 8: Effects of Dissolution Temperature and Time on the Solubility of Nimodipine 1. Prescription

TABLE 9

Prescription design

| Components | Temperature 20° C. | 30° C. | 40° C. | 50° C. | 60° C. | 70° C. | 80° C. | 90° C. | 100° C. |
|---|---|---|---|---|---|---|---|---|---|
| Nimodipine | 60 mg | 60 mg | 60 mg | 60 mg | 60 mg | 60 mg | 60 mg | 60 mg | 60 mg |
| Ethanol | 1.2 mL | 1.2 mL | 1.2 mL | 1.2 mL | 1.2 mL | 1.2 mL | 1.2 mL | 1.2 mL | 1.2 mL |
| Sulfobutyl ether-β-Cyclodextrin | 12 g | 12 g | 12 g | 12 g | 12 g | 12 g | 12 g | 12 g | 12 g |
| Water for injection | Filling to 30 mL | | | | | | | | |

2. Preparation Process

Sulfobutyl ether-β-cyclodextrin (12 g, parallel 9 groups) was added, an appropriate amount of water for injection was added, and the mixture was stirred to dissolve to obtain a sulfobutyl ether-β-cyclodextrin aqueous solution; a total of 60 mg of nimodipine was dissolved in 1.2 mL of ethanol under stirring conditions. The nimodipine ethanol solution was added to the sulfobutyl ether-β-cyclodextrin aqueous solution and stirred at 20° C., 30° C., 40° C., 50° C., 60° C., 70° C., 80° C., 90° C., and 100° C. for 5 h, and the points were taken at 1 h, 2 h, 3 h, 4 h, and 5 h. The obtained solution was filtered through a 0.45 μm polyethersulfone filter membrane, and the content of nimodipine was detected via HPLC.

3. Results Analysis

The content of nimodipine cyclodextrin taken at different times was determined. The results are as follows.

TABLE 10

Solubility of nimodipine stirred for 5 h at different temperatures

| Time | Temperature concentration(mg/ml) 20° C. | 30° C. | 40° C. | 50° C. | 60° C. | 70° C. | 80° C. | 90° C. | 100° C. |
|---|---|---|---|---|---|---|---|---|---|
| 1 h | 0.56 | 1.06 | 1.07 | 1.14 | 1.18 | 1.20 | 1.43 | 1.70 | 1.78 |
| 2 h | 0.40 | 1.03 | 1.05 | 1.10 | 1.17 | 1.21 | 1.44 | 1.72 | 1.90 |
| 3 h | 0.38 | 0.75 | 0.81 | 1.08 | 1.15 | 1.25 | 1.46 | 1.74 | 1.93 |
| 4 h | 0.35 | 0.54 | 0.60 | 0.97 | 1.13 | 1.26 | 1.47 | 1.77 | 1.95 |
| 5 h | 0.32 | 0.41 | 0.49 | 0.96 | 1.12 | 1.29 | 1.49 | 1.78 | 1.99 |

TABLE 11

The ratio of sulfobutyl ether-β-cyclodextrin to nimodipine stirred at different temperatures for 5 h

| | Temperature Excipient ratio | | | | | | | | |
|---|---|---|---|---|---|---|---|---|---|
| Time | 20° C. | 30° C. | 40° C. | 50° C. | 60° C. | 70° C. | 80° C. | 90° C. | 100° C. |
| 1 h | 714 | 377 | 374 | 351 | 339 | 333 | 280 | 235 | 225 |
| 2 h | 1000 | 388 | 381 | 364 | 342 | 331 | 278 | 233 | 211 |
| 3 h | 1053 | 533 | 494 | 370 | 348 | 320 | 274 | 230 | 207 |
| 4 h | 1143 | 741 | 667 | 412 | 354 | 317 | 272 | 226 | 205 |
| 5 h | 1250 | 976 | 816 | 417 | 357 | 310 | 268 | 225 | 201 |

The results showed that with increasing temperature, the solubility of nimodipine increased, and the excipient ratio decreased. In the case of low temperature, with increasing stirring time, the solubility of nimodipine decreased, and the excipient ratio increased. This finding indicates that increasing the temperature is beneficial for the inclusion of nimodipine by sulfobutyl ether-β-cyclodextrin, but too high a temperature may lead to the production of related substances.

Example 9: Preparation of Nimodipine for Injection

1. Prescription

| | |
|---|---|
| Nimodipine | 3 mg |
| Ethanol | 0.06 mL |
| Sulfobutyl ether-β-cyclodextrin | 3 g |
| Water for injection | Filling to 30 mL |

2. Preparation Process

Three grams of sulfobutyl ether-β-cyclodextrin were dissolved in an appropriate amount of water for injection at 20° C. to obtain a sulfobutyl ether-β-cyclodextrin aqueous solution. Three milligrams of nimodipine was dissolved in 0.06 mL of ethanol, and then the nimodipine ethanol solution was added to the sulfobutyl ether-β-cyclodextrin aqueous solution under stirring conditions. The mixture was stirred for 10 minutes, and then, water for injection was added to make up to 30 mL. The resulting solution was sterilely filtered through a 0.22 μm microporous membrane, packed, freeze-dried, nitrogen-filled, and packaged. Clean and dry $N_2$ was introduced throughout the dissolution and filtration process.

Example 10: Preparation of Nimodipine for Injection

1. Prescription

| | |
|---|---|
| Nimodipine | 15 mg |
| Ethanol | 0.3 mL |
| Sulfobutyl ether-β-cyclodextrin | 6 g |
| Water for injection | Filling to 30 mL |

2. Preparation Process

Sulfobutyl ether-β-cyclodextrin (6 g) was added, an appropriate amount of water for injection was added, and the mixture was stirred at 40° C. to dissolve to obtain a sulfobutyl ether-β-cyclodextrin aqueous solution; 15 mg of nimodipine was dissolved in 0.3 mL of ethanol. An ethanol solution of nimodipine was added to an aqueous solution of sulfobutyl ether-β-cyclodextrin under stirring conditions. The solution was stirred for 30 min, and the water for injection was added to bring the volume to 30 mL. The obtained solution was sterilely filtered through a 0.22 μm microporous membrane, filled and freeze-dried, packaged, and obtained.

Example 11: Preparation of Nimodipine for Injection

1. Prescription

| | |
|---|---|
| Nimodipine | 15 mg |
| Sulfobutyl ether-β-cyclodextrin | 10.5 g |
| Sodium citrate | 60 mg |
| Citric acid | 9 mg |
| Water for injection | Filling to 30 mL |

2. Preparation Process

Sulfobutyl ether-β-cyclodextrin (10.5 g), sodium citrate (60 mg) and citric acid (9 mg) were added to an appropriate amount of water for injection and stirred at 60° C. to dissolve to obtain a sulfobutyl ether-β-cyclodextrin aqueous solution. Nimodipine (15 mg) was added to an aqueous solution of sulfobutyl ether-β-cyclodextrin under stirring conditions, the mixture was stirred for 2 h, and water for injection was added to reach a volume of 30 mL. The obtained solution was sterilely filtered through a 0.22 μm microporous membrane, filled, freeze-dried, filled with nitrogen, packaged, and obtained. Clean and dry $N_2$ was introduced throughout the dissolution and filtration process.

Example 12: Preparation of Nimodipine for Injection

1. Prescription

| | |
|---|---|
| Nimodipine | 24 mg |
| Ethanol | 0.48 mL |
| Sulfobutyl ether-β-cyclodextrin | 9 g |
| Water for injection | Filling to 30 mL |

2. Preparation Process

Sulfobutyl ether-β-cyclodextrin (9 g) was added, an appropriate amount of water for injection was added, and the mixture was stirred at 50° C. to dissolve to obtain a sulfobutyl ether-β-cyclodextrin aqueous solution, 24 mg of nimodipine was dissolved in 0.48 ml of ethanol. Under stirring conditions, the nimodipine ethanol solution was added to the sulfobutyl ether-β-cyclodextrin aqueous solution, the mixture was stirred for 1 h, and 30 mL of injection water was added. The solution was sterilely filtered through a 0.22 μm microporous membrane, filled, freeze-dried, filled with nitrogen, packaged, and obtained. Clean and dry $N_2$ was introduced throughout the dissolution and filtration process.

Example 13: Preparation of Nimodipine for Injection

1. Prescription

| | |
|---|---|
| Nimodipine | 24 mg |
| Ethanol | 0.3 mL |
| Sulfobutyl ether-β-cyclodextrin | 10.8 g |
| Water for injection | Filling to 30 mL |

2. Preparation Process

A total of 10.8 g of sulfobutyl ether-β-cyclodextrin was added to an appropriate amount of water for injection and stirred at 60° C. to dissolve to obtain a sulfobutyl ether-β-cyclodextrin aqueous solution. Twenty-four milligrams of nimodipine was dissolved in 0.3 mL of ethanol. An ethanol solution of nimodipine was added to a sulfobutyl ether-β-cyclodextrin aqueous solution under stirring conditions, the mixture was stirred for 1 h, and the water for injection was added to a final volume of 30 mL. The obtained solution was sterilely filtered through a 0.22 μm microporous membrane, filled, freeze-dried, and packaged.

Example 14: Preparation of Nimodipine for Injection

1. Prescription

| | |
|---|---|
| Nimodipine | 24 mg |
| Sulfobutyl ether-β-cyclodextrin | 12 g |
| Disodium hydrogen phosphate | 709 mg |
| Citric acid | 102 mg |
| Water for Injection | Make up to 30 mL |

2. Preparation Process

Sulfobutyl ether-β-cyclodextrin (12 g), disodium hydrogen phosphate (709 mg) and citric acid (102 mg) were added, an appropriate amount of water for injection was added, stirred at 70° C. to dissolve, and a sulfobutyl ether-β-cyclodextrin aqueous solution was obtained. Nimodipine (24 mg) was added, and under stirring conditions, nimodipine was added to the sulfobutyl ether-β-cyclodextrin aqueous solution, which was stirred for 2 h, and water for injection was added to make up 30 mL. The resulting solution was sterilely filtered through a 0.22 μm microporous membrane, filled and freeze-dried and packaged.

Example 15: Preparation of Nimodipine for Injection

1. Prescription

| | |
|---|---|
| Nimodipine | 30 mg |
| Ethanol | 0.3 mL |
| Sulfobutyl ether-β-cyclodextrin | 9 g |
| Water for Injection | Make up to 30 mL |

2. Preparation Process

Nine grams of sulfobutyl ether-β-cyclodextrin was added, an appropriate amount of water for injection was added, the mixture was stirred at 50° C. to dissolve, and a sulfobutyl ether-β-cyclodextrin aqueous solution was obtained; 30 mg of nimodipine was added, 0.3 mL of ethanol was added, the ethanol solution of nimodipine was added to the sulfobutyl ether-β-cyclodextrin aqueous solution under stirring conditions, the mixture was stirred for 2 h, water for injection was added to make up to 30 mL. The resulting solution was filtered through a 0.22 μm microporous filter membrane, filled, freeze-dried, filled with nitrogen and packaged. Clean and dry $N_2$ was introduced throughout the dissolution and filtration process.

Example 16: Preparation of Nimodipine for Injection

1. Prescription

| | |
|---|---|
| Nimodipine | 30 mg |
| Ethanol | 0.3 mL |
| Sulfobutyl ether-β-cyclodextrin | 9.9 g |
| Disodium hydrogen phosphate | 520 mg |
| Sodium dihydrogen phosphate | 281 mg |
| Water for Injection | Make up to 30 mL |

2. Preparation Process

A total of 9.9 g of sulfobutyl ether-β-cyclodextrin, 520 mg of disodium hydrogen phosphate and 281 mg of sodium dihydrogen phosphate were combined, an appropriate amount of water for injection was added, and the mixture was stirred at 60° C. to dissolve the mixture to obtain an aqueous sulfobutyl ether-β-cyclodextrin solution. A total of 30 mg of nimodipine was added, 0.3 mL of ethanol was added for dissolution, and then an ethanol solution of nimodipine was added to the aqueous sulfobutyl ether-β-cyclodextrin solution with stirring. After 1 h, water for injection was added to reach a volume of 30 mL, and the resulting solution was filtered through a 0.22 μm microporous membrane, filled, freeze-dried, packaged, and then obtained.

Example 17: Preparation of Nimodipine for Injection

| | |
|---|---|
| Nimodipine | 30 mg |
| Ethanol | 0.48 mL |
| Sulfobutyl ether-β-cyclodextrin | 11.1 g |
| Water for Injection | Make up to 30 mL |

2. Preparation Process

A total of 11.1 g of sulfobutyl ether-β-cyclodextrin was added, an appropriate amount of water for injection was added, the mixture was stirred at 60° C. to dissolve, and a sulfobutyl ether-β-cyclodextrin aqueous solution was obtained; 30 mg of nimodipine was added, 0.48 mL of ethanol was added, the mixture was dissolved, the nimodipine ethanol solution was added to the sulfobutyl ether-β-cyclodextrin aqueous solution under stirring conditions, the mixture was stirred for 2 h, and water for injection was added to reach a volume of 30 mL. The resulting solution was sterilely filtered through a 0.22 μm microporous membrane, filled, freeze-dried, nitrogen-filled and packaged. Clean and dry $N_2$ was introduced throughout the dissolution and filtration process.

Example 18: Preparation of Nimodipine for Injection

1. Prescription

| | |
|---|---|
| Nimodipine | 30 mg |
| Ethanol | 0.48 mL |
| Sulfobutyl ether-β-cyclodextrin | 9 g |
| Sodium citrate | 60 mg |
| Citric acid | 9 mg |
| Water for Injection | Make up to 30 mL |

2. Preparation Process

Nine grams of sulfobutyl ether-β-cyclodextrin, 60 mg of sodium citrate and 9 mg of citric acid were added, an appropriate amount of water for injection was added, and the mixture was stirred at 60° C. to dissolve the mixture to obtain an aqueous sulfobutyl ether-β-cyclodextrin solution. Thirty milligrams of nimodipine was added, 0.48 mL of ethanol was dissolved, an ethanol solution of nimodipine was added to the aqueous solution of sulfobutyl ether-β-cyclodextrin solution under stirring conditions, and the mixture was stirred for 3 h. Water for injection was added to reach 30 mL, and the resulting solution was filtered through a 0.22 μm microporous filter membrane, freeze-dried, nitrogen-filled and packaged. The resulting solution was sterilely filtered through a 0.22 μm microporous membrane, filled, freeze-dried, nitrogen-filled and packaged. Clean and dry $N_2$ was introduced throughout the dissolution and filtration process.

Example 19: Preparation of Nimodipine for Injection

1. Prescription

| | |
|---|---|
| Nimodipine | 30 mg |
| Ethanol | 0.72 mL |
| Sulfobutyl ether-β-cyclodextrin | 9 g |
| Water for Injection | Make up to 30 mL |

2. Preparation Process

Nine grams of sulfobutyl ether-β-cyclodextrin was added, an appropriate amount of water for injection was added, the mixture was stirred at 100° C. to dissolve, and a sulfobutyl ether-β-cyclodextrin aqueous solution was obtained; 30 mg of nimodipine was added, 0.72 mL of ethanol was added, the ethanol solution of nimodipine was added to the sulfobutyl ether-β-cyclodextrin aqueous solution under stirring conditions, the mixture was stirred for 2 h, water for injection was added to make up to 30 mL. The resulting solution was sterilely filtered through a 0.22 μm microporous filter membrane, filled, freeze-dried and packaged.

Example 20: Preparation of Nimodipine for Injection

1. Prescription

| | |
|---|---|
| Nimodipine | 30 mg |
| Ethanol | 0.48 mL |
| Sulfobutyl ether-β-cyclodextrin | 10.5 g |
| Water for Injection | Make up to 30 mL |

2. Preparation Process

A total of 10.5 g of sulfobutyl ether-β-cyclodextrin was added, and an appropriate amount of water for injection was added. The mixture was stirred at 50° C. to dissolve, and a sulfobutyl ether-β-cyclodextrin aqueous solution was obtained. Thirty milligrams of nimodipine was added, 0.48 mL of ethanol was added, and the mixture was dissolved. Then, a nimodipine ethanol solution was added to a sulfobutyl ether-β-cyclodextrin aqueous solution under stirring, which was stirred for 5 h. Water for injection was added to make up to 30 mL. The resulting solution was sterilely filtered through a 0.22 μm microporous filter membrane, filled, freeze-dried and packaged, i.e., obtained.

Example 21: Preparation of Nimodipine for Injection

1. Prescription

| | |
|---|---|
| Nimodipine | 30 mg |
| Ethanol | 0.72 mL |
| Sulfobutyl ether-β-cyclodextrin | 10.5 g |
| Water for Injection | Make up to 30 mL |

2. Preparation Process

A total of 10.5 g of sulfobutyl ether-β-cyclodextrin was added, an appropriate amount of water for injection was added, the mixture was stirred at 60° C. to dissolve, and a sulfobutyl ether-β-cyclodextrin aqueous solution was obtained. A total of 30 mg of nimodipine was added, 0.72 mL of ethanol was added, the mixture was dissolved, an ethanol nimodipine solution was added to a sulfobutyl ether-β-cyclodextrin aqueous solution under stirring conditions, the mixture was stirred for 1 hour, and then, water for injection was added to make up to 30 mL. The resulting solution was sterilely filtered through a 0.22 μm microporous filter membrane, filled, freeze-dried and packaged, i.e., obtained.

Example 22: Preparation of Nimodipine for Injection

1. Prescription

| | |
|---|---|
| Nimodipine | 30 mg |
| Ethanol | 0.9 mL |
| Sulfobutyl ether-β-cyclodextrin | 10.5 g |
| Water for Injection | Make up to 30 mL |

2. Preparation Process

A total of 10.5 g of sulfobutyl ether-β-cyclodextrin was added, and an appropriate amount of water for injection was added. The mixture was stirred at 70° C. to dissolve, and a sulfobutyl ether-β-cyclodextrin aqueous solution was obtained. A total of 30 mg of nimodipine was added, 0.9 mL of ethanol was added, and the mixture was dissolved. A nimodipine ethanol solution was added to a sulfobutyl ether-β-cyclodextrin aqueous solution under stirring, which was stirred for 2 h, and water for injection was added until it reached 30 mL. The resulting solution was sterilely filtered through a 0.22 μm microporous filter membrane, filled, freeze-dried, filled with nitrogen and packaged. Clean and dry $N_2$ was introduced throughout the dissolution and filtration process.

Example 23: Preparation of Nimodipine for Injection

1. Prescription

| | |
|---|---|
| Nimodipine | 30 mg |
| Sulfobutyl ether-β-cyclodextrin | 10.5 g |
| Water for Injection | Make up to 30 mL |

2. Preparation Process

Sulfobutyl ether-β-cyclodextrin (10.5 g) was added, an appropriate amount of water for injection was added, stirred at 80° C. to dissolve, and a sulfobutyl ether-β-cyclodextrin aqueous solution was obtained. Nimodipine (30 mg) was added, and under stirring, nimodipine was added to the sulfobutyl ether-β-cyclodextrin aqueous solution, stirred for 3 h, and water for injection was added to make up to 30 mL. The resulting solution was filtered sterilely through a 0.22 μm microporous filter membrane, filled, freeze-dried, nitrogen-filled and packaged, and then obtained. Clean and dry $N_2$ was introduced throughout the dissolution and filtration process.

Example 24: Preparation of Nimodipine for Injection

1. Prescription

| | |
|---|---|
| Nimodipine | 30 mg |
| Ethanol | 0.9 mL |
| Sulfobutyl ether-β-cyclodextrin | 12 g |
| Water for Injection | Make up to 30 mL |

2. Preparation Process

Sulfobutyl ether-β-cyclodextrin (12 g) was added, an appropriate amount of water for injection was added, the mixture was stirred at 60° C. to dissolve, and a sulfobutyl ether-β-cyclodextrin aqueous solution was obtained; 30 mg of nimodipine was added, 0.9 mL of ethanol was added to dissolve, and under stirring conditions, a nimodipine ethanol solution was added to the sulfobutyl ether-β-cyclodextrin aqueous solution stirred for 2 h, water for injection was added to reach 30 mL. The resulting solution was sterilely filtered through a 0.22 μm microporous filter membrane, filled, freeze-dried and packaged, i.e., obtained.

Example 25: Preparation of Nimodipine for Injection

1. Prescription

| | |
|---|---|
| Nimodipine | 30 mg |
| Sulfobutyl ether-β-cyclodextrin | 12 g |
| Disodium hydrogen phosphate | 520 mg |
| Sodium dihydrogen phosphate | 281 mg |
| Water for Injection | Make up to 30 mL |

2. Preparation Process

Sulfobutyl ether-β-cyclodextrin (12 g), disodium hydrogen phosphate (520 mg), and sodium dihydrogen phosphate (281 mg) were added, an appropriate amount of water for injection was added, stirred at 60° C. to dissolve the mixture, a sulfobutyl ether-β-cyclodextrin aqueous solution was added, and a total of 30 mg of nimodipine was taken. Under stirring conditions, nimodipine was added to the sulfobutyl ether-β-cyclodextrin aqueous solution, stirred for 2 h, and water for injection was added to make up to 30 mL. The resulting solution was sterilely filtered through a 0.22 μm microporous filter membrane, filled, freeze-dried and packaged.

Example 26: Preparation of Nimodipine for Injection

1. Prescription

| | |
|---|---|
| Nimodipine | 30 mg |
| Ethanol | 0.48 mL |
| Sulfobutyl ether-β-cyclodextrin | 13.5 g |
| Water for Injection | Make up to 30 mL |

2. Preparation Process

A total of 13.5 g of sulfobutyl ether-β-cyclodextrin was added, an appropriate amount of water for injection was added, the mixture was stirred at 50° C. to dissolve, and a sulfobutyl ether-β-cyclodextrin aqueous solution was obtained; 30 mg of nimodipine was added, 0.48 mL of ethanol was added, the mixture was dissolved, a nimodipine ethanol solution was added to the sulfobutyl ether-β-cyclodextrin aqueous solution under stirring conditions, the mixture was stirred for 3 hours, and water for injection was added to reach a volume of 30 mL. Then, the resulting solution was sterilely filtered through a 0.22 μm microporous filter membrane, filled, freeze-dried and packaged.

Example 27: Preparation of Nimodipine for Injection

1. Prescription

| | |
|---|---|
| Nimodipine | 36 mg |
| Ethanol | 0.72 mL |
| Sulfobutyl ether-β-cyclodextrin | 12 g |
| Water for Injection | Make up to 30 mL |

2. Preparation Process

Sulfobutyl ether-β-cyclodextrin (12 g) was added, an appropriate amount of water for injection was added, and the mixture was stirred at 70° C. to dissolve the mixture. A total of 36 mg of nimodipine was added, 0.72 mL of ethanol was added to dissolve the mixture, a nimodipine ethanol solution was added to the sulfobutyl ether-β-cyclodextrin aqueous solution under stirring conditions, the mixture was stirred for 3 h, and water for injection was added to reach 30 mL. The resulting solution was sterilely filtered through a 0.22 μm microporous filter membrane, filled, freeze-dried and packaged.

Example 28: Preparation of Nimodipine for Injection

1. Prescription

| | |
|---|---|
| Nimodipine | 36 mg |
| Ethanol | 0.72 mL |
| Sulfobutyl ether-β-cyclodextrin | 12.6 g |
| Disodium hydrogen phosphate | 59 mg |
| Potassium dihydrogen phosphate | 6.7 mg |
| Water for Injection | Make up to 30 mL |

2. Preparation Process

Sulfobutyl ether-β-cyclodextrin (12.6 g), disodium hydrogen phosphate (59 mg) and potassium dihydrogen phosphate (6.7 mg) were added, an appropriate amount of water for injection was added, the mixture was stirred at 60° C. to dissolve the mixture, a sulfobutyl ether-β-cyclodextrin aqueous solution was obtained; nimodipine (36 mg) was added, 0.72 mL of ethanol was added, and the ethanol solution of nimodipine was added to the aqueous sulfobutyl ether-β-cyclodextrin solution with stirring. The mixture was stirred for 2 h, water for injection was added to reach 30 mL, and then the solution was sterilely filtered through a 0.22 μm microporous filter membrane, filled, freeze-dried and packaged.

Example 29: Preparation of Nimodipine for Injection

1. Prescription

| | |
|---|---|
| Nimodipine | 36 mg |
| Sulfobutyl ether-β-cyclodextrin | 13.5 g |
| Water for Injection | Make up to 30 mL |

2. Preparation Process

A total of 13.5 g of sulfobutyl ether-β-cyclodextrin was added, an appropriate amount of water for injection was added, the mixture was stirred at 100° C. to dissolve, a sulfobutyl ether-β-cyclodextrin aqueous solution was obtained. 36 mg of nimodipine was added, nimodipine was added to the sulfobutyl ether-β-cyclodextrin aqueous solution under stirring, the mixture was stirred for 1 h, water for injection was added to reach 30 mL, and then the solution was filtered sterilely through a 0.22 μm microporous filter membrane, filled, freeze-dried, nitrogen-filled and packaged. Clean and dry $N_2$ was introduced throughout the dissolution and filtration process.

Example 30: Preparation of Nimodipine for Injection

1. Prescription

| | |
|---|---|
| Nimodipine | 45 mg |
| Ethanol | 0.9 mL |
| Sulfobutyl ether-β-cyclodextrin | 13.5 g |
| Water for Injection | Make up to 30 mL |

2. Preparation Process

A total of 13.5 g of sulfobutyl ether-β-cyclodextrin was added, an appropriate amount of water for injection was added, the mixture was stirred at 80° C. to dissolve, and a sulfobutyl ether-β-cyclodextrin aqueous solution was obtained; 45 mg of nimodipine was added, 0.9 mL of ethanol was added, the mixture was dissolved, an ethanol nimodipine solution was added to a sulfobutyl ether-β-cyclodextrin aqueous solution under stirring conditions, the mixture was stirred for 4 h, water for injection was added to make up to 30 mL, and then the obtained solution was sterilely filtered through a 0.22 μm microporous filter membrane, filled, freeze-dried and packaged.

Example 31: Preparation of Nimodipine for Injection

1. Prescription

| | |
|---|---|
| Nimodipine | 60 mg |
| Ethanol | 1.5 mL |
| Sulfobutyl ether-β-cyclodextrin | 15 g |
| Water for Injection | Make up to 30 mL |

2. Preparation Process

A total of 15 g of sulfobutyl ether-β-cyclodextrin was added, an appropriate amount of water for injection was added, and the mixture was stirred at 100° C. to dissolve, resulting in a sulfobutyl ether-β-cyclodextrin aqueous solution; 60 mg of nimodipine was added, and 1.5 mL of ethanol was added to dissolve the mixture. Then, the mixture was stirred, an ethanol solution of nimodipine was added to the aqueous sulfobutyl ether-β-cyclodextrin solution, the mixture was stirred for 5 h, and water for injection was added to make up to 30 mL. The resulting solution was sterilely filtered through a 0.22 μm microporous filter membrane, filled, freeze-dried, nitrogen-filled and packaged. Clean and dry $N_2$ was introduced throughout the dissolution and filtration process.

Example 32: Preparation of Nimodipine for Injection

1. Prescription

| | |
|---|---|
| Nimodipine | 60 mg |
| Ethanol | 0.9 mL |
| Sulfobutyl ether-β-cyclodextrin | 12 g |
| potassium dihydrogen phosphate | 204 mg |
| Sodium hydroxide | 3.5 mg |
| Water for Injection | Make up to 30 mL |

2. Preparation Process

A total of 12 g of sulfobutyl ether-β-cyclodextrin, 204 mg of potassium dihydrogen phosphate and 3.5 mg of sodium hydroxide were added, an appropriate amount of water for injection was added, and the mixture was stirred at 100° C. until it dissolved to obtain an aqueous sulfobutyl ether-β-cyclodextrin solution. A total of 60 mg of nimodipine was added, 0.9 mL of ethanol was added for dissolution, an ethanol solution of nimodipine was added to the aqueous sulfobutyl ether-β-cyclodextrin solution under stirring, the mixture was stirred for 5 h, and water for injection was added to make up to 30 mL. The resulting solution was sterilely filtered through a 0.22 μm microporous filter membrane, filled, freeze-dried, packaged, and then obtained.

Example 33: Determination of Ethanol Residue in Nimodipine for Injection

Nimodipine for injection prepared in Examples 9, 10, 12, 13, 15, 16, 17, 18, 19, 20, 21, 22, 24, 26, 27, 28, 30, 31, and 32 was selected, and the ethanol residue was tested.

1. The ethanol content of nimodipine for injection was determined according to the method of determination of residual solvents (the second method of the Chinese Pharmacopoeia 2020 edition of the four general rules 0861), as follows:

Chromatographic Conditions:

A DB-624 capillary column was used as the chromatographic column; the programmed temperature was increased, the starting temperature was 70° C., maintained for 2 min, increased to 120° C. at a rate of 10° C. per minute, increased to 220° C. at a rate of 20° C. per minute, and maintained for 3 min; the shunt ratio was 20:1; the flow rate of the column was 1 mL/min; the temperature of the injection port was 200° C.; the temperature of the detector was 250° C.; and the equilibrium temperature of the headspace vial was 80° C.; and the equilibrium time was 30 min.

Preparation of the Blank Solution:

Two grams of lyophilized powder of the prepared blank auxiliaries were weighed in three 20 mL volumetric flasks, diluted to scale with DMF, shaken well, precisely measured to 4 mL and sealed in a headspace bottle and then sealed.

Preparation of the Control Solution:

An appropriate amount of ethanol was weighed precisely and diluted with DMF to make a solution containing 5 mg per 1 mL, which was used as the control solution. Specifically, 2 mL of the control reserve solution was added to a 20 mL volumetric flask, which was diluted with DMF to scale, shaken well, and 4 mL was precisely measured. The mixture was then placed in a headspace bottle and sealed, that is, the control solution was obtained.

Preparation of Test Solution:

Two grams of nimodipine were weighed for injection, placed in three 20 mL volumetric flasks, diluted with DMF to scale, shaken well, and 4 mL was measured precisely. The mixture was placed in a headspace bottle and sealed, and the test mixture was obtained.

Determination Method:

The blank solution and the control solution were added to the headspace, and the chromatograms were recorded. The test solution and the control solution were subsequently added to the headspace, the chromatograms were recorded, and the peak areas were calculated according to the external standard method.

2. Experimental results

TABLE 12

Ethanol residue results of nimodipine for injection

| Sample name | Ethanol residue (%) |
|---|---|
| Nimodipine for injection (Example 9) | 0.16 |
| Nimodipine for injection (Example 10) | 0.29 |
| Nimodipine for injection (Example 12) | 0.24 |
| Nimodipine for injection (Example 13) | 0.02 |
| Nimodipine for injection (Example 15) | 0.12 |
| Nimodipine for injection (Example 16) | 0.02 |
| Nimodipine for injection (Example 17) | 0.03 |
| Nimodipine for injection (Example 18) | 0.02 |
| Nimodipine for injection (Example 19) | 0.01 |
| Nimodipine for injection (Example 20) | 0.03 |
| Nimodipine for injection (Example 21) | 0.08 |
| Nimodipine for injection (Example 22) | 0.06 |
| Nimodipine for injection (Example 24) | 0.04 |
| Nimodipine for injection (Example 26) | 0.07 |
| Nimodipine for injection (Example 27) | 0.03 |
| Nimodipine for injection (Example 28) | 0.04 |
| Nimodipine for injection (Example 30) | 0.02 |
| Nimodipine for injection (Example 31) | 0.03 |
| Nimodipine for injection (Example 32) | 0.02 |

The results showed that the ethanol residue of nimodipine used for injection in the present study met the quality standard requirements through the control of temperature and time.

Example 34: Dilution Stability Study of Nimodipine for Injection

1. Experimental Method

Nimodipine for injection prepared according to Example 21 and nimodipine injection were separately diluted with 0.9% sodium chloride injection and 5% glucose to clinical administration concentrations. The samples were observed and collected at 0, 3, 6, 9, 12, and 24 hours after dilution. After filtration through a 0.45 μm polyethersulfone filter membrane, the nimodipine content was determined via the aforementioned assay method.

2. Experimental Results

Table 13 shows the changes in nimodipine content after dilution with 0.9% sodium chloride injection for nimodipine for injection and nimodipine injection (Nimotop®).

| Time(h) | Sample Name | Content (%) | Appearance |
|---|---|---|---|
| 0 | Nimotop ® | 98.87 | − |
| | Nimodipine for Injection | 99.78 | − |
| 3 | Nimotop ® | 33.65 | + |
| | Nimodipine for Injection | 100.31 | − |
| 6 | Nimotop ® | 7.81 | + |
| | Nimodipine for Injection | 99.81 | − |
| 9 | Nimotop ® | 5.42 | + |
| | Nimodipine for Injection | 99.01 | − |
| 12 | Nimotop ® | 3.36 | + |
| | Nimodipine for Injection | 98.27 | − |
| 24 | Nimotop ® | 2.30 | + |
| | Nimodipine for Injection | 99.34 | − |

Note:
− indicates no precipitation,
+ indicates precipitation

TABLE 14

Changes in the contents of nimodipine after dilution with 5% dextrose for nimodipine for injection and nimodipine injection (Nimotop ®)

| Time(h) | Sample Name | Content (%) | Appearance |
|---|---|---|---|
| 0 | Nimotop ® | 99.24 | − |
| | Nimodipine for Injection | 99.76 | − |
| 3 | Nimotop ® | 44.64 | + |
| | Nimodipine for Injection | 100.18 | − |
| 6 | Nimotop ® | 14.32 | + |
| | Nimodipine for Injection | 100.06 | − |
| 9 | Nimotop ® | 9.46 | + |
| | Nimodipine for Injection | 99.34 | − |
| 12 | Nimotop ® | 8.13 | + |
| | Nimodipine for Injection | 99.94 | − |
| 24 | Nimotop ® | 6.24 | + |
| | Nimodipine for Injection | 98.79 | − |

Note:
− indicates no precipitation,
+ indicates precipitation.

Nimodipine injection by 0.9% sodium chloride or 5% dextrose dilution, 3 h that is, a large number of drug precipitations, resulted in a significant decrease in content; 24 h after the content reached only 2.30% and 6.24%, respectively, the dilution stability was very poor; the nimodipine for injection of the present disclosure by 0.9% sodium chloride injection or 5% dextrose dilution, 24 h after the content did not significantly change, the appearance was clear, and the dilution stability is good. The above results show that, compared with Nimotop®, the dilution stability of nimodipine for injection of the present disclosure is obviously improved, with obvious advantages.

Example 35: Hemolytic Study of Nimodipine for Injection

1. Experimental Method

Nimodipine for injection prepared according to Example 21 and commercially available nimodipine injection were diluted separately with 0.9% sodium chloride injection to a clinical dosing concentration of 0.04 mg/mL. Eight 10 mL clean glass test tubes were numbered as follows: Tubes 1 to 5 contained different concentrations of nimodipine for injection, Tube 6 served as a negative control, Tube 7 served as a positive control, and Tube 8 served as a commercially available Nimotop®. As per the table below, 2% red blood cell suspension, 0.9% sodium chloride injection, distilled water, and the respective test solutions were sequentially added, mixed thoroughly, and immediately placed in a water bath at 37±0.5° C. for incubation. Hemolysis in each tube was observed and recorded every 15 minutes initially and subsequently every hour for a total of 3 hours.

TABLE 15

Table of hemolysis experimental design.

| Tube number | 1 | 2 | 3 | 4 | 5 | 6 | 7 | 8 |
|---|---|---|---|---|---|---|---|---|
| 2% red blood cell suspension (mL) | 2.5 | 2.5 | 2.5 | 2.5 | 2.5 | 2.5 | 2.5 | 2.5 |
| 0.9% sodium chloride injection(mL) | 2.0 | 2.1 | 2.2 | 2.3 | 2.4 | 2.5 | | 2.0 |
| Distilled water(mL) | | | | | | | 2.5 | |
| Nimodipine for Injection(mL) | 0.5 | 0.4 | 0.3 | 0.2 | 0.1 | | | |
| Nimotop ®(mL) | | | | | | | | 0.5 |

2. Experimental Results

Figure 2:
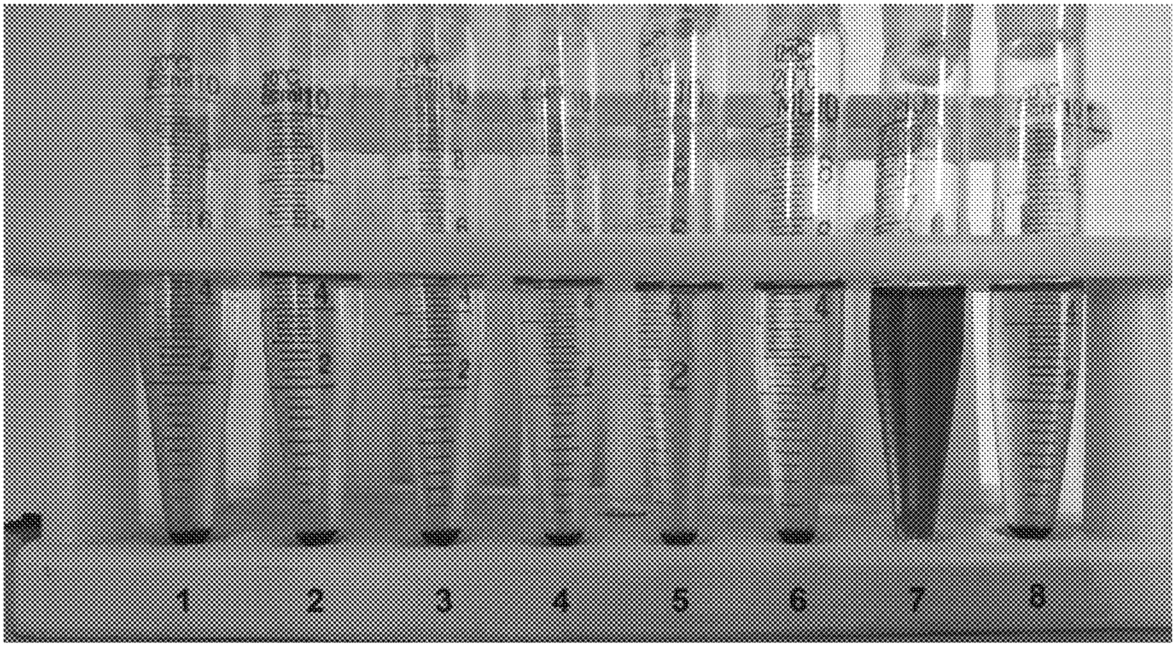
FIG. 2 Diagram of the hemolytic effect of nimodipine for injection.

The hemolysis results are shown in FIG. 2. Nimodipine for Injection described in this disclosure (Tubes 1-5) showed no signs of hemolysis, indicating good safety of Nimodipine for Injection in this disclosure.

Example 36: High-Temperature Stability Study of Nimodipine for Injection

Nimodipine for injection prepared according to Example 21 was subjected to storage at 60° C. for 1 month to assess changes in drug content and relevant impurities.

1. The analytical method for identifying related substances in nimodipine in this disclosure was performed via high-performance liquid chromatography (HPLC) according to the Chinese Pharmacopoeia of the four general rules (2020 edition, General Chapter 0512) under light-protected conditions.

Chromatographic conditions and system suitability test: Cis column (250×4.6 mm, 5 μm) with octadecyl silane-bonded silica gel as the filler; mobile phase consisting of methanol-acetonitrile-water (35:38:27, v/v/v); detection wavelength at 235 nm; and injection volume of 10 μL. The separation between the nimodipine peak and the peaks of impurities B, C, and I in the system suitability chromatogram should be greater than 3.0.

Figure 3:
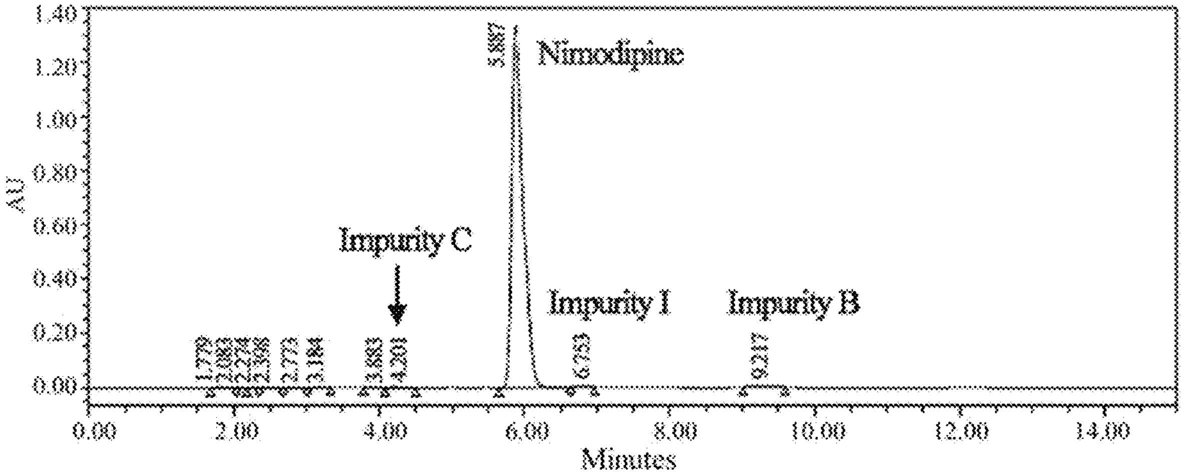
FIG. 3 HPLC chromatogram of the test solution for the determination of the substance of interest.

Preparation of the test solution: An appropriate amount of the sample was accurately weighed and diluted with the mobile phase to prepare a solution containing approximately 0.2 mg of nimodipine per 1 mL. The HPLC chromatograms of the related substances in the test solution are shown in FIG. 3.

To prepare the reference solution, 1 mL of the test solution was accurately measured, transferred to a 100 mL volumetric flask, diluted to volume with the mobile phase, and mixed thoroughly.

Preparation of the impurity I reference solution: The impurity I reference standard was accurately weighed and diluted with the mobile phase to prepare a solution containing approximately 1 μg of impurity I per 1 mL.

Preparation of the system suitability solution: Appropriate amounts of nimodipine and impurity B, C, and I reference standards were taken, dissolved in the mobile phase, and diluted to prepare a mixed solution containing approximately 200 μg and 1 μg per 1 mL.

Analytical procedure: The test solution, Impurity I reference solution, and reference solution were accurately measured, and the samples were injected into the HPLC system. If impurity peaks are present in the test solution chromatogram, peaks with retention times consistent with those of impurity I, except for those with relative retention times less than 0.45, are quantified via the peak area via the external standard method. Other individual impurities are quantified via the self-reference method.

2. Experimental Results

Table 16 presents the results of the high-temperature stability experiment of nimodipine for injection.

| Sample Name | Time (Days) | Properties | Content (%) | Related substances (%) Impurity B | Impurity C | Impurity I | Other Impurities | Total impurities |
|---|---|---|---|---|---|---|---|---|
| Nimodipine for Injection | 0 | Slightly yellow loose lumps | 98.45 | 0.28 | 0.11 | not detected | not detected | 0.39 |
| (Example 21) | 30 | Slightly yellow loose lumps | 99.80 | 0.29 | 0.12 | not detected | not detected | 0.41 |

2. Results Analysis

After storing nimodipine for injection at 60° C. in a stability chamber for 1 month, the labeled content of nimodipine showed almost no change, and related substances met the specified limits. These results indicate that the nimodipine for injection described in this disclosure has good high-temperature stability and meets the quality requirements.

Example 37: Effect of Preparation Temperature and Time on the Solubility of Nimodipine in Sulfobutyl Ether-β-Cyclodextrin Using the nimodipine content and related substances as indicators, the effects of the preparation temperature and time on the solubility of nimodipine in sulfobutyl ether-β-cyclodextrin and related substances were investigated.

1. Prescription

TABLE 17

| Prescription design | | | | | | | | | |
|---|---|---|---|---|---|---|---|---|---|
| | Temperature | | | | | | | | |
| Components | 20° C. | 30° C. | 40° C. | 50° C. | 60° C. | 70°° C. | 80° C. | 90° C. | 100° C. |
| Nimodipine | 60 mg | 60 mg | 60 mg | 60 mg | 60 mg | 60 mg | 60 mg | 60 mg | 60 mg |
| Sulfobutyl ether-β-cyclodextrin | 12 g | 12 g | 12 g | 12 g | 12 g | 12 g | 12 g | 12 g | 12 g |
| Water for Injection | Make up to 30 mL | | | | | | | | |

2. Preparation Process

Twelve grams of sulfobutyl ether-β-cyclodextrin was added, and the mixture was divided into 9 parallel groups. An appropriate amount of water for injection was added, and the mixture was stirred until dissolved to obtain a sulfobutyl ether-β-cyclodextrin aqueous solution. Sixty milligrams of nimodipine was added to a sulfobutyl ether-β-cyclodextrin aqueous solution with stirring at a speed of 2.0 m/s. The mixture was stirred for 5 h at temperatures of 20° C., 30° C., 40° C., 50° C., 60° C., 70° C., 80° C., 90° C., and 100° C. Samples were taken at 1, 2, 3, 4, and 5 hours. The resulting solutions were filtered through 0.45 μm polyethersulfonefilter membranes and analyzed via HPLC to determine the content of nimodipine and related substances.

3. Experimental Results

The contents and related substances of the nimodipine cyclodextrin inclusion complexes at different times are summarized below.

TABLE 18

| Solubility of nimodipine in sulfobutyl ether-β-cyclodextrin at different temperatures with 5 hours of stirring | | | | | | | | | |
|---|---|---|---|---|---|---|---|---|---|
| | Temperature Concentration (mg/mL) | | | | | | | | |
| Time | 20° C. | 30° C. | 40° C. | 50° C. | 60° C. | 70° C. | 80° C. | 90° C. | 100° C. |
| 1 h | 0.23 | 0.42 | 0.66 | 0.81 | 1.01 | 1.14 | 1.31 | 1.46 | 1.62 |
| 2 h | 0.25 | 0.45 | 0.68 | 0.83 | 1.05 | 1.19 | 1.36 | 1.53 | 1.66 |
| 3 h | 0.28 | 0.48 | 0.69 | 0.87 | 1.09 | 1.24 | 1.41 | 1.56 | 1.69 |
| 4 h | 0.29 | 0.50 | 0.73 | 0.91 | 1.12 | 1.26 | 1.44 | 1.59 | 1.74 |
| 5 h | 0.32 | 0.53 | 0.75 | 0.93 | 1.15 | 1.29 | 1.48 | 1.65 | 1.79 |

TABLE 19

| Proportion of sulfobutyl ether-β-cyclodextrin to nimodipine at different temperatures after 5 h of stirring | | | | | | | | | |
|---|---|---|---|---|---|---|---|---|---|
| | Temperature Excipient ratio | | | | | | | | |
| Time | 20° C. | 30° C. | 40° C. | 50° C. | 60° C. | 70° C. | 80° C. | 90° C. | 100° C. |
| 1 h | 1739 | 952 | 606 | 494 | 396 | 351 | 305 | 274 | 247 |
| 2 h | 1600 | 889 | 588 | 482 | 381 | 336 | 294 | 261 | 241 |
| 3 h | 1429 | 833 | 580 | 460 | 367 | 323 | 284 | 256 | 237 |
| 4 h | 1379 | 800 | S48 | 440 | 357 | 317 | 278 | 252 | 230 |
| 5 h | 1250 | 755 | 533 | 430 | 348 | 310 | 270 | 242 | 223 |

TABLE 20

| Related substances of nimodipine in cyclodextrin complexes after 5 hours of stirring at different temperatures | | | | | | |
|---|---|---|---|---|---|---|
| Temperature (° C.) | Related substances (%) | Time 1 h | 2 h | 3 h | 4 h | 5 h |
| 50 | Impurity B | 0.13 | 0.14 | 0.14 | 0.14 | 0.15 |
| | Impurity C | 0.22 | 0.24 | 0.24 | 0.24 | 0.25 |
| | Impurity I | not detected | not detected | not detected | not detected | no detected |
| | Other impurities | not detected | not detected | not detected | not detected | 0.07 |
| | Total impurities | 0.35 | 0.38 | 0.38 | 0.38 | 0.47 |
| 60 | Impurity B | 0.15 | 0.15 | 0.15 | 0.15 | 0.17 |
| | Impurity C | 0.23 | 0.24 | 0.26 | 0.26 | 0.26 |
| | Impurity I | not detected | not detected | not detected | not detected | not detected |
| | Other impurities | not detected | 0.06 | 0.07 | 0.07 | 0.07 |
| | Total impurities | 0.38 | 0.45 | 0.48 | 0.48 | 0.50 |
| 70 | Impurity B | 0.16 | 0.17 | 0.17 | 0.17 | 0.18 |
| | Impurity C | 0.25 | 0.25 | 0.26 | 0.27 | 0.27 |
| | Impurity I | not detected | not detected | not detected | not detected | not detected |
| | Other impurities | 0.07 | 0.08 | 0.09 | 0.10 | 0.10 |
| | Total impurities | 0.48 | 0.50 | 0.52 | 0.54 | 0.55 |
| 80 | Impurity B | 0.17 | 0.17 | 0.17 | 0.16 | 0.18 |
| | Impurity C | 0.27 | 0.27 | 0.27 | 0.28 | 0.28 |
| | Impurity I | not detected | not detected | not detected | not detected | 0.04 |
| | Other impurities | 0.09 | 0.10 | 0.14 | 0.15 | 0.16 |
| | Total impurities | 0.53 | 0.54 | 0.58 | 0.59 | 0.66 |

TABLE 20-continued

| Related substances of nimodipine in cyclodextrin complexes after 5 hours of stirring at different temperatures | | | | | | |
|---|---|---|---|---|---|---|
| Temperature (° C.) | Related substances (%) | Time 1 h | 2 h | 3 h | 4 h | 5 h |
| 90 | Impurity B | 0.17 | 0.17 | 0.18 | 0.19 | 0.18 |
| | Impurity C | 0.27 | 0.27 | 0.26 | 0.29 | 0.29 |
| | Impurity 1 | not detected | not detected | not detected | not detected | 0.05 |
| | Other impurities | 0.10 | 0.11 | 0.15 | 0.17 | 0.24 |
| | Total impurities | 0.54 | 0.55 | 0.59 | 0.65 | 0.71 |
| 100 | Impurity B | 0.18 | 0.18 | 0.18 | 0.19 | 0.19 |
| | Impurity C | 0.28 | 0.28 | 0.28 | 0.29 | 0.29 |
| | Impurity I | not detected | 0.04 | 0.05 | 0.06 | 0.06 |
| | Other impurities | 0.12 | 0.14 | 0.17 | 0.20 | 0.21 |
| | Total impurities | 0.58 | 0.64 | 0.68 | 0.74 | 0.75 |

The experiment revealed that without the addition of ethanol, the solubility of nimodipine increased with increasing temperature and stirring time, whereas the excipient ratio decreased. However, the contents of the related substances of nimodipine increase with increasing temperature and stirring time. Therefore, selecting an appropriate preparation temperature and time is crucial for preparing nimodipine sulfobutyl ether-β-cyclodextrin inclusion complexes.

Example 38: Effect of Stirring Speed on the Solubility of Nimodipine in Sulfobutyl Ether-β-Cyclodextrin 1. Prescription

TABLE 21

| Prescription design | | | | | | | | |
|---|---|---|---|---|---|---|---|---|
| | Stirring speed (m/s) | | | | | | | |
| Components | 0.25 | 0.5 | 1.0 | 1.5 | 2.0 | 3.0 | 6.0 | 10.0 |
| Nimodipine | 50 mg | 50 mg | 50 mg | 50 mg | 50 mg | 50 mg | 50 mg | 50 mg |
| Sulfobutyl ether-β-cyclodextrin | 25 g | 25 g | 25 g | 25 g | 25 g | 25 g | 25 g | 25 g |
| Water for Injection | Make up to 100 mL | | | | | | | |

2. Preparation Process

A total of 25 g of sulfobutyl ether-β-cyclodextrin was added to 8 parallel groups. An appropriate amount of water for injection was added, and the mixture was stirred at 75° C. until it was dissolved, resulting in an aqueous solution of sulfobutyl ether-β-cyclodextrin. Subsequently, 50 mg of nimodipine was added to the sulfobutyl ether-β-cyclodextrin solution under stirring at speeds of 0.25 m/s, 0.5 m/s, 1.0 m/s, 1.5 m/s, 2.0 m/s, 3.0 m/s, 6.0 m/s, and 10.0 m/s for 1.5 hours. Water for injection was added to a volume of 100 mL, and the resulting solution was filtered through a 0.45 μm polyethersulfone filter membrane. Nimodipine content was analyzed via HPLC.

3. Experimental Results

The effects of stirring speed on the solubility of nimodipine in sulfobutyl ether-β-cyclodextrin are shown in Table 22. These results indicate that the drug content increases with increasing stirring speed, and too low a stirring speed may not achieve the desired drug loading concentration.

TABLE 22

Effects of stirring speed on the solubility of nimodipine in sulfobutyl ether-β-cyclodextrin

| Check projects | Stirring speed (m/s) 0.25 | 0.5 | 1.0 | 1.5 | 2.0 | 3.0 | 6.0 | 10.0 |
|---|---|---|---|---|---|---|---|---|
| Drug content (mg/mL) | 0.188 | 0.312 | 0.430 | 0.494 | 0.502 | 0.496 | 0.499 | 0.498 |
| Percentage content (%) | 37.60 | 62.49 | 85.94 | 98.84 | 100.31 | 99.26 | 99.86 | 99.67 |

4. Discussion

This study demonstrated that the stirring speed significantly affects the inclusion efficiency of sulfobutyl ether-β-cyclodextrin with nimodipine. Higher stirring speeds lead to better inclusion efficiency and higher drug content. Interestingly, we unexpectedly found through experimentation that, even without the addition of ethanol as a cosolvent, adjusting the stirring speed can achieve relatively ideal drug loading concentrations. Stirring speed is one of the crucial core technologies of this disclosure; therefore, we have included protection for stirring speed in the claims.

Example 39: Effect of the Excipient Ratio on the Dilution Stability of Nimodipine Cyclodextrin Inclusion Complexes 1. Prescription

TABLE 23

Prescription Design

| Components | Sulfobutyl ether-β-cyclodextrin dosage 15% | 17.5% | 20% | 22.5% | 25% | 30% | 35% |
|---|---|---|---|---|---|---|---|
| Nimodipine | 50 mg | 50 mg | 50 mg | 50 mg | 50 mg | 50 mg | 50 mg |
| Sulfobutyl ether-β-cyclodextrin | 15 g | 17.5 g | 20 g | 22.5 g | 25 g | 30 g | 35 g |
| Water for Injection | Make up to 100 mL | | | | | | |

2. Preparation Process

First, 15 g. 17.5 g, 20 g, 22.5 g, 25 g, 30 g, and 35 g of sulfobutyl ether-β-cyclodextrin were taken separately. an appropriate amount of water for injection was added, and the mixture was stirred at 75° C. until dissolved, resulting in solutions of sulfobutyl ether-β-cyclodextrin. Then, 50 mg of nimodipine was added to each sulfobutyl ether-β-cyclodextrin aqueous solution under stirring at a speed of 1.8 m/s for 1.5 hours. Water for injection was added to reach a volume of 100 mL. The resulting solutions were sterilely filtered through a 0.22 μm microporous filter membrane, filled, freeze-dried, and packaged.

The prepared nimodipine for injection was diluted with 0.9% sodium chloride to a drug concentration of 0.2 mg/mL. The samples were observed and collected at 0, 12, 24, 36, 48, and 60 hours. After filtration through a 0.45 μm polyethersulfone filter membrane, the nimodipine content was determined via the aforementioned analytical method.

3. Experimental Results

The results of dilution stability are shown in Table 24. When the excipient ratio was ≥350, the dilution stability time of nimodipine for injection could reach more than 24 h. When the excipient ratio was ≥400, the dilution stability time of nimodipine for injection could reach more than 36 h. When the excipient ratio was ≥450, the dilution stability time of nimodipine for injection could reach more than 48 h. When the excipient ratio was ≥500, the dilution stability time of nimodipine for injection could reach more than 60 h. The results showed that the excipient ratio significantly affected the dilution stability of the nimodipine cyclodextrin inclusion complex.

TABLE 24

Dilution stability of nimodipine cyclodextrin inclusion complexes with different excipient ratios.

| Excipient Ratio | Dilution Stability Conditions |
|---|---|
| 300 | 12 h content decreased significantly, stabilization time < 12 h |
| 350 | 24 h content almost no change, stabilization time > 24 h |
| 400 | 36 h content almost no change, 36 h < stabilization time < 48 h |

TABLE 24-continued

| Dilution stability of nimodipine cyclodextrin inclusion complexes with different excipient ratios. | |
|---|---|
| Excipient Ratio | Dilution Stability Conditions |
| 450 | 48 h content almost changed, stabilization time > 48 h |
| 500 | 60 h content almost variable, stabilization time > 60 h |
| 600 | 60 h content almost variable, stabilization time > 60 h |
| 700 | 60 h content almost variable, stabilization time > 60 h |

4. Discussion

The study results indicate that the dilution stability time of nimodipine cyclodextrin inclusion complexes increases with increasing excipient ratios. According to the recommended dosing regimen on the product label, the maximum duration for administering Nimotop® (250 mL: 50 mg) is 51 hours. This study revealed that when the excipient ratio is ≥500 in nimodipine cyclodextrin inclusion complexes, the dilution stability time can exceed 60 hours, meeting clinical usage requirements. For these reasons, we have increased the range of the claimed mass ratios of sulfobutyl ether-β-cyclodextrin and nimodipine.

Example 40: Preparation of Nimodipine for Injection

1. Prescription

| | |
|---|---|
| Nimodipine | 3 mg |
| Ethanol | 0.07 mL |
| Sulfobutyl ether-β-cyclodextrin | 3 g |
| Water for injection | Make up to 30 mL |

2. Preparation Process

Three grams of sulfobutyl ether-β-cyclodextrin were dissolved in a suitable amount of water for injection at 70° C. with stirring until dissolution, and a sulfobutyl ether-β-cyclodextrin aqueous solution was obtained. Three milligrams of nimodipine were dissolved in 0.07 mL of ethanol. Under stirring at a speed of 3.0 m/s, the nimodipine-ethanol solution was added to the sulfobutyl ether-β-cyclodextrin aqueous solution, which was stirred for 10 minutes. Water for injection was added to bring the total volume to 30 mL. The resulting solution was sterilely filtered through a 0.22 μm microporous filter membrane, filled, freeze-dried, and then packaged.

Example 41: Preparation of Nimodipine for Injection

1. Prescription

| | |
|---|---|
| Nimodipine | 6 mg |
| Ethanol | 0.15 mL |
| Sulfobutyl ether-β-cyclodextrin | 3 g |
| Water for injection | Make up to 30 mL |

2. Preparation Process

Three grams of sulfobutyl ether-β-cyclodextrin was dissolved in a suitable amount of water for injection at 60° C. with stirring until dissolution, and a sulfobutyl ether-β-cyclodextrin aqueous solution was obtained. Six milligrams of nimodipine was taken. Under stirring at a speed of 2.0 m/s, the nimodipine-ethanol solution was added to the sulfobutyl ether-β-cyclodextrin aqueous solution, which was stirred for 30 minutes. Water for injection was added to bring the total volume to 30 mL. The resulting solution was sterilely filtered through a 0.22 μm microporous filter membrane, filled into containers, subjected to freeze-drying, and then packaged.

Example 42: Preparation of Nimodipine for Injection

1. Prescription

| | |
|---|---|
| Nimodipine | 6 mg |
| Sulfobutyl ether-β-cyclodextrin | 3 g |
| Water for injection | Make up to 30 mL |

2. Preparation Process

Three grams of sulfobutyl ether-β-cyclodextrin was dissolved in a suitable amount of water for injection at 20° C. with stirring until dissolution, and a sulfobutyl ether-β-cyclodextrin aqueous solution was obtained. Six milligrams of nimodipine was added to the sulfobutyl ether-β-cyclodextrin aqueous solution under stirring at a speed of 10.0 m/s. The mixture was stirred for 4 hours, and water for injection was added to bring the total volume to 30 mL. The resulting solution was sterilely filtered through a 0.22 μm microporous filter membrane, filled into containers, subjected to freeze-drying, and then packaged.

Example 43: Preparation of Nimodipine for Injection

1. Prescription

| | |
|---|---|
| Nimodipine | 11.25 mg |
| Sulfobutyl ether-β-cyclodextrin | 4.5 g |
| Sodium citrate | 60 mg |
| Citric acid | 9 mg |
| Water for injection | Make up to 30 mL |

2. Preparation Procedure

A total of 4.5 g of sulfobutyl ether-β-cyclodextrin, 60 mg of sodium citrate and 9 mg of citric acid were added, an appropriate amount of water for injection was added, and the mixture was stirred at 90° C. to dissolve to obtain an aqueous sulfobutyl ether-β-cyclodextrin solution; 11.25 mg of nimodipine was added, nimodipine was added to the aqueous sulfobutyl ether-β-cyclodextrin solution, the stirring speed was 0.5 m/s, the mixture was stirred for 3 h, water for injection was added to make up to 30 mL.

Example 44: Preparation of Nimodipine for Injection

1. Prescription:

| | |
|---|---|
| Nimodipine | 12 mg |
| Sulfobutyl ether-β-cyclodextrin | 6 g |
| Water for injection | Make up to 30 mL |

2. Preparation Process:

Sulfobutyl ether-β-cyclodextrin (6 g) was added, an appropriate amount of water for injection was added, stirred at 70° C. to dissolve, and a sulfobutyl ether-β-cyclodextrin aqueous solution was obtained. Nimodipine (12 mg) was added, and the mixture was stirred at a speed of 2.0 m/s. Nimodipine was added to the sulfobutyl ether-β-cyclodextrin aqueous solution, which was stirred for 3 h, and water for injection was added to make up to 30 mL. The resulting solution was sterilely filtered through a 0.22 μm microporous filter membrane, which was filled, freeze-dried, nitrogen-filled, and packaged, and obtained. Clean and dry $N_2$ was introduced throughout the dissolution and filtration process.

Example 45: Preparation of Nimodipine for Injection

1. Prescription

| | |
|---|---|
| Nimodipine | 12 mg |
| Sulfobutyl ether-β-cyclodextrin | 6 g |
| Water for injection | Make up to 30 mL |

2. Preparation Process

Sulfobutylether-β-cyclodextrin (6 g) was dissolved in a suitable amount of water for injection at 85° C. with stirring until completely dissolved, resulting in an aqueous solution of sulfobutylether-β-cyclodextrin. Nimodipine (12 mg) was then added to the sulfobutyl ether-β-cyclodextrin aqueous solution under stirring at 0.8 m/s for 2 hours. Water for injection was added to adjust the volume to 30 mL. The resulting solution was sterilely filtered through a 0.22 μm microporous filter membrane, filled into containers, freeze-dried, and packaged to obtain the final product.

Example 46: Preparation of Nimodipine for Injection

1. Prescription

| | |
|---|---|
| Nimodipine | 14 mg |
| Sulfobutyl ether-β-cyclodextrin | 6.3 g |
| Disodium hydrogen phosphate | 709 mg |
| Citric acid | 102 mg |
| Water for injection | Make up to 30 mL |

2. Preparation Process

Sulfobutyl ether-β-cyclodextrin (6.3 g), disodium hydrogen phosphate (709 mg) and citric acid (102 mg) were added, an appropriate amount of water for injection was added, and the mixture was stirred at 40° C. to dissolve the mixture, resulting in a sulfobutyl ether-β-cyclodextrin aqueous solution. Under a stirring speed of 6.0 m/s, nimodipine (14 mg) was added to aqueous sulfobutyl ether-β-cyclodextrin, the mixture was stirred for 3 h, water for injection was added to reach a volume of 30 mL, and then the solution was sterilely filtered through a 0.22 μm microporous filter membrane, filled, freeze-dried and packaged.

Example 47: Preparation of Nimodipine for Injection

1. Prescription

| | |
|---|---|
| Nimodipine | 14.67 mg |
| Ethanol | 0.3 mL |
| Sulfobutyl ether-β-cyclodextrin | 6.6 g |
| Water for injection | Make up to 30 mL |

2. Preparation Process

A total of 6.6 g of sulfobutyl ether-β-cyclodextrin was added, an appropriate amount of water for injection was added, the mixture was stirred at 60° C. to dissolve, and a sulfobutyl ether-β-cyclodextrin aqueous solution was obtained; 14.67 mg of nimodipine was added, 0.3 mL of ethanol was added, the mixture was dissolved, a nimodipine ethanol solution was added to the sulfobutyl ether-β-cyclodextrin aqueous solution under a stirring speed of 2.0 m/s, the mixture was stirred for 2 h, and water for injection was added to make up to 30 mL. The resulting solution was sterilely filtered through a 0.22 μm microporous filter membrane, filled, freeze-dried, filled with nitrogen, and packaged, and the resulting solution was obtained. Clean and dry $N_2$ was introduced throughout the dissolution and filtration process.

Example 48: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, the mixture was stirred at 75° C. for dissolution to obtain a sulfobutyl ether-β-cyclodextrin aqueous solution. 15 mg of nimodipine was taken. When the stirring speed was 1.8 m/s, nimodipine was added to the sulfobutyl ether-β-cyclodextrin aqueous solution, which was stirred for 1.5 h, and water for injection was added to make up to 30 mL. The resulting solution was sterilely filtered through a 0.22 μm microporous filter membrane, filled, freeze-dried and packaged.

Example 49: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, stirred at 80° C. to dissolve, and a sulfobutyl ether-β-cyclodextrin aqueous solution was obtained. Nimodipine (15 mg) was added, the stirring speed was 1.7 m/s, nimodipine was added to the sulfobutyl ether-β-cyclodextrin aqueous solution, the mixture was stirred for 2 h, water for injection was added to make up to 30 mL, and the resulting solution was sterilely filtered through a 0.22 μm microporous filter membrane, filled, freeze-dried and packaged.

Example 50: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, stirred at 90° C. to dissolve, and a sulfobutyl ether-β-cyclodextrin aqueous solution was obtained. Nimodipine (15 mg) was added, and the stirring speed was 1.5 m/s. Nimodipine was added to the sulfobutyl ether-β-cyclodextrin aqueous solution, which was stirred for 1 h, and water for injection was added to make up to 30 mL. The resulting solution was sterilely filtered through a 0.22 μm microporous filter membrane, filled, freeze-dried and packaged.

Example 51: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, stirred at 75° C. to dissolve, and a sulfobutyl ether-β-cyclodextrin aqueous solution was obtained. Nimodipine (15 mg) was added, and the stirring speed was 1.9 m/s. Nimodipine was added to the sulfobutyl ether-β-cyclodextrin aqueous solution, which was stirred for 1.5 h, and water for injection was added to reach 30 mL. The resulting solution was sterilely filtered through a 0.22 μm microporous filter membrane, filled, freeze-dried and packaged.

Example 52: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, stirred at 65° C. to dissolve, and a sulfobutyl ether-β-cyclodextrin aqueous solution was obtained. Nimodipine (15 mg) was added, the stirring speed was 2.0 m/s, nimodipine was added to the sulfobutyl ether-β-cyclodextrin aqueous solution, the mixture was stirred for 2 h, water for injection was added to make up to 30 mL, and the resulting solution was sterilely filtered through a 0.22 μm microporous filter membrane, filled, freeze-dried and packaged.

Example 53: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, stirred at 75° C. to dissolve, and a sulfobutyl ether-β-cyclodextrin aqueous solution was obtained. Nimodipine (15 mg) was added. Nimodipine was added to the sulfobutyl ether-β-cyclodextrin aqueous solution at a stirring speed of 2.5 m/s, which was stirred for 3 h, and water for injection was added to make up to 30 mL. The resulting solution was sterilely filtered through a 0.22 μm microporous filter membrane, filled, freeze-dried and packaged.

Example 54: Preparation of Nimodipine for Injection

1. Prescription

| | |
|---|---|
| Nimodipine | 15 mg |
| Sulfobutyl ether-β-cyclodextrin | 7.5 g |
| Water for injection | Make up to 30 mL |

2. Preparation Process

Sulfobutyl ether-β-cyclodextrin (7.5 g) was added, an appropriate amount of water for injection was added, stirred at 60° C. to dissolve, and a sulfobutyl ether-β-cyclodextrin aqueous solution was obtained. Nimodipine (15 mg) was added, the stirring speed was 3 m/s, nimodipine was added to the sulfobutyl ether-β-cyclodextrin aqueous solution, the mixture was stirred for 3 h, water for injection was added to make up to 30 mL, and the resulting solution was sterile filtered through a 0.22 μm microporous filter membrane, filled, freeze-dried and packaged.

Example 55: Preparation of Nimodipine for Injection

1. Prescription

| | |
|---|---|
| Nimodipine | 15 mg |
| Ethanol | 0.45 mL |
| Sulfobutyl ether-β-cyclodextrin | 7.5 g |
| Water for injection | Make up to 30 mL |

2. Preparation Process

A total of 7.5 g of sulfobutyl ether-β-cyclodextrin was added, an appropriate amount of water for injection was added, the mixture was stirred at 70° C. to dissolve, and a sulfobutyl ether-β-cyclodextrin aqueous solution was obtained. Fifteen milligrams of nimodipine was added, 0.45 mL of ethanol was added to dissolve, nimodipine was added to the aqueous solution of sulfobutyl ether-β-cyclodextrin at a stirring speed of 2.0 m/s, the mixture was stirred for 1 hour, and then, water for injection was added to reach 30 mL. The solution was sterilely filtered through a 0.22 μm microporous filter membrane, filled, freeze-dried and packaged.

Example 56: Preparation of Nimodipine for Injection

1. Prescription

| | |
|---|---|
| Nimodipine | 18 mg |
| Ethanol | 0.75 mL |
| Sulfobutyl ether-β-cyclodextrin | 9 g |
| Water for injection | Make up to 30 mL |

2. Preparation Process

Nine grams of sulfobutyl ether-β-cyclodextrin was added, an appropriate amount of water for injection was added, the mixture was stirred at 90° C. to dissolve, and a sulfobutyl ether-β-cyclodextrin aqueous solution was obtained; 18 mg of nimodipine was added, 0.75 mL of ethanol was added, and the mixture was dissolved. Then, the mixture was stirred at a stirring speed of 1.0 m/s, an ethanol solution of nimodipine was added to the aqueous sulfobutyl ether-β-cyclodextrin solution, the mixture was stirred for 3 h, and water for injection was added to make up to 30 mL. The solution was sterilely filtered through a 0.22 μm microporous filter membrane, filled, freeze-dried and packaged.

Example 57: Preparation of Nimodipine for Injection

1. Prescription

| | |
|---|---|
| Nimodipine | 18 mg |
| Sulfobutyl ether-β-cyclodextrin | 9 g |
| Water for injection | Make up to 30 mL |

2. Preparation Process

Sulfobutyl ether-β-cyclodextrin (9 g) was added, an appropriate amount of water for injection was added, stirred at 75° C. to dissolve, and a sulfobutyl ether-β-cyclodextrin aqueous solution was obtained; 18 mg of nimodipine was added, and the stirring speed was 3 m/s. Nimodipine was added to the sulfobutyl ether-β-cyclodextrin aqueous solution, which was stirred for 2 h, water for injection was added to make up to 30 mL, and the resulting solution was sterilely filtered through a 0.22 μm microporous filter membrane, filled, freeze-dried and packaged. Clean and dry $N_2$ was introduced throughout the dissolution and filtration process.

Example 58: Preparation of Nimodipine for Injection

1. Prescription

| | |
|---|---|
| Nimodipine | 19.10 mg |
| Sulfobutyl ether-β-cyclodextrin | 10.5 g |
| Water for injection | Make up to 30 mL |

2. Preparation Process

Sulfobutyl ether-β-cyclodextrin (10.5 g) was added, an appropriate amount of water for injection was added, stirred at 40° C. to dissolve, and a sulfobutyl ether-β-cyclodextrin aqueous solution was obtained. Nimodipine (19.10 mg) was added, and when the stirring speed was 6.0 m/s, nimodipine was added to the sulfobutyl ether-β-cyclodextrin aqueous solution, which was stirred for 5 h, water for injection was added to reach 30 mL, and the resulting solution was sterilely filtered through a 0.22 μm microporous filter membrane, filled, freeze-dried and packaged.

Example 59: Preparation of Nimodipine for Injection

1. Prescription

| | |
|---|---|
| Nimodipine | 20.72 mg |
| Sulfobutyl ether-β-cyclodextrin | 11.4 g |
| $KH_2PO_4$ | 204 mg |
| NaOH | 3.5 mg |
| Water for injection | Make up to 30 mL |

2. Preparation Process

A total of 11.4 g of sulfobutyl ether-β-cyclodextrin, 204 mg of potassium dihydrogen phosphate and 3.5 mg of sodium hydroxide were added, an appropriate amount of water for injection was added, and the mixture was stirred at 90° C. to dissolve the mixture to obtain a sulfobutyl ether-β-cyclodextrin aqueous solution. A total of 20.72 mg of nimodipine was added, the stirring speed was 1.0 m/s, nimodipine was added to the aqueous sulfobutyl ether-β-cyclodextrin, the mixture was stirred for 2 h, and then, water for injection was added to a final volume of 30 mL. The resulting solution was sterilely filtered through a 0.22 μm microporous filter membrane, filled, freeze-dried and packaged, and it was obtained.

Example 60: Preparation of Nimodipine for Injection

1. Prescription

| | |
|---|---|
| Nimodipine | 30 mg |
| Sulfobutyl ether-β-cyclodextrin | 12 g |
| Water for injection | Make up to 30 mL |

2. Preparation Process

Sulfobutyl ether-β-cyclodextrin (12 g) was added, an appropriate amount of water for injection was added, stirred at 95° C. to dissolve, and a sulfobutyl ether-β-cyclodextrin aqueous solution was obtained. Nimodipine (30 mg) was added, the stirring speed was 0.8 m/s, nimodipine was added to the sulfobutyl ether-β-cyclodextrin aqueous solution, the mixture was stirred for 4 h, water for injection was added to make up to 30 mL, and the resulting solution was sterile filtered through a 0.22 μm microporous membrane, filled, freeze-dried and packaged.

Example 61: Preparation of Nimodipine for Injection

1. Prescription

| | |
|---|---|
| Nimodipine | 30 mg |
| Sulfobutyl ether-β-cyclodextrin | 12 g |
| Water for injection | Make up to 30 mL |

2. Preparation Process

Sulfobutyl ether-β-cyclodextrin (12 g) was added, an appropriate amount of water for injection was added, stirred at 80° C. to dissolve, and a sulfobutyl ether-β-cyclodextrin aqueous solution was obtained. Nimodipine (30 mg) was added, the stirring speed was 2.0 m/s, nimodipine was added to the sulfobutyl ether-β-cyclodextrin aqueous solution, the mixture was stirred for 3 h, water for injection was added to make up to 30 mL, and the resulting solution was sterile filtered through a 0.22 μm microporous filter membrane, filled, freeze-dried, filled with nitrogen and packaged. Clean and dry $N_2$ was introduced throughout the dissolution and filtration process.

Example 62: Preparation of Nimodipine for Injection

| | |
|---|---|
| Nimodipine | 22.5 mg |
| Sulfobutyl ether-β-cyclodextrin | 13.5 g |
| Water for injection | Make up to 30 mL |

2. Preparation Process

Sulfobutyl ether-β-cyclodextrin (13.5 g) was added, an appropriate amount of water for injection was added, stirred at 75° C. to dissolve, and a sulfobutyl ether-β-cyclodextrin aqueous solution was obtained. Nimodipine (22.5 mg) was added, and the stirring speed was 3.0 m/s. Nimodipine was added to the sulfobutyl ether-β-cyclodextrin aqueous solution, which was stirred for 2 h, and water for injection was added to make up to 30 mL. The resulting solution was sterilely filtered through a 0.22 μm microporous filter membrane, filled, freeze-dried and packaged.

Example 63: Preparation of Nimodipine for Injection

1. Prescription

| | |
|---|---|
| Nimodipine | 42 mg |
| Ethanol | 1.05 mL |
| Sulfobutyl ether-β-cyclodextrin | 15 g |
| Water for injection | Make up to 30 mL |

2. Preparation Process

A total of 15 g of sulfobutyl ether-β-cyclodextrin was added, an appropriate amount of water for injection was added, the mixture was stirred at 100° C. to dissolve, and a sulfobutyl ether-β-cyclodextrin aqueous solution was obtained; 42 mg of nimodipine was added, and 1.05 mL of ethanol was added, after which it was dissolved. Then, the mixture was stirred at a stirring speed of 1.7 m/s, an ethanol solution of nimodipine was added to the aqueous sulfobutyl ether-β-cyclodextrin solution, the mixture was stirred for 1.5 h, and water for injection was added to make up to 30 mL. The solution was sterilely filtered through a 0.22 μm microporous filter membrane, filled, freeze-dried and packaged.

Example 64: Preparation of Nimodipine for Injection

| | |
|---|---|
| Nimodipine | 21.43 mg |
| Sulfobutyl ether-β-cyclodextrin | 15 g |
| Water for injection | Make up to 30 mL |

2. Preparation Process

Sulfobutyl ether-β-cyclodextrin (15 g) was added, an appropriate amount of water for injection was added, stirred at 95° C. to dissolve, and a sulfobutyl ether-β-cyclodextrin aqueous solution was obtained. Nimodipine (21.43 mg) was added, and the stirring speed was 2.0 m/s. Nimodipine was added to the sulfobutyl ether-β-cyclodextrin aqueous solution, which was stirred for 2 h, and water for injection was added to make up to 30 mL. The resulting solution was sterilely filtered through a 0.22 μm microporous filter membrane, filled, freeze-dried and packaged. Clean and dry $N_2$ was introduced throughout the dissolution and filtration process.

Example 65: Determination of Ethanol Residue in Nimodipine for Injection

1. Experimental Methods

Nimodipine for injection prepared in Examples 40, 41, 47, 55, 56 and 63 were selected and tested for ethanol residue. The ethanol content of nimodipine for injection was determined according to the method for determination of residual solvents (Chinese Pharmacopoeia 2020 version of the four general rules 0861, the second method).

2. Results

TABLE 25

Ethanol residue results of nimodipine for injection

| Sample name | Ethanol residue (%) |
|---|---|
| Nimodipine for injection (Example 40) | 0.03 |
| Nimodipine for injection (Example 41) | 0.03 |
| Nimodipine for injection (Example 47) | 0.04 |
| Nimodipine for injection (Example 55) | 0.06 |
| Nimodipine for injection (Example 56) | 0.09 |
| Nimodipine for injection (Example 63) | 0.15 |

The results showed that by controlling the temperature and time, the ethanol residue of the nimodipine for injection used in the present study was low.

Example 66: Dilution Stability Study of Nimodipine for Injection

1. Experimental Methods

Nimodipine for injection prepared in Example 48 solubilized with water for injection and nimodipine injection were diluted with 0.9% sodium chloride injection and 5% dextrose to a clinical concentration of 0.04 mg/mL. The content of nimodipine was determined via the above method after filtration with a 0.45 μm polyethersulfone filter membrane, and the points were observed at 0, 3, 6, 9, 12 and 24 h.

2. Results

Figure 4:
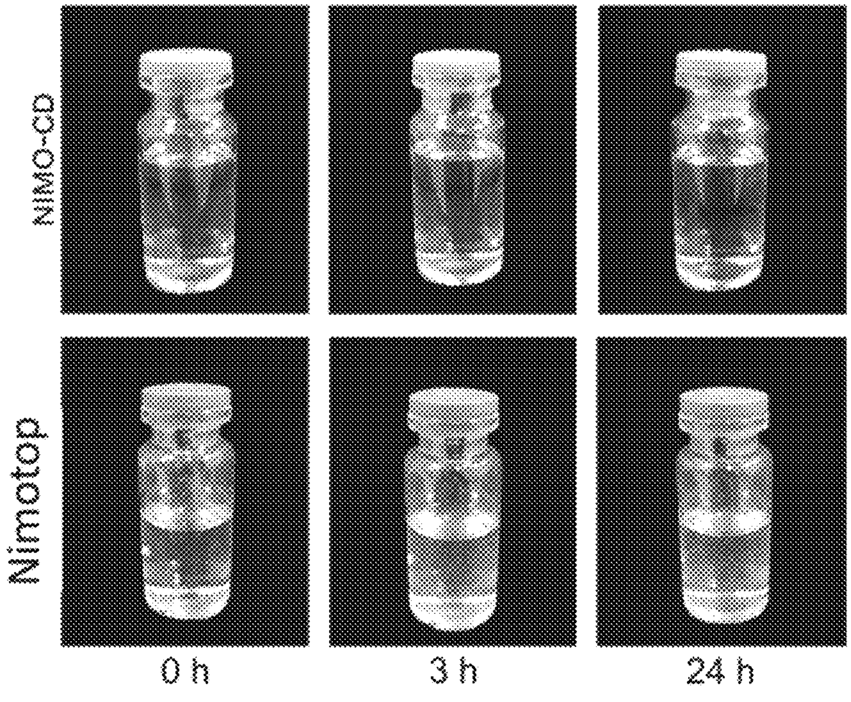
FIG. 4 Dilution stability diagram of nimodipine for injection and Nimotop®.

The stability results of nimodipine for injection and nimodipine injection diluted with 0.9% sodium chloride are shown in Tables 26 and 27, and the appearance of the solutions is shown in FIG. 4.

TABLE 26

Changes in the content of nimodipine for injection and nimodipine injection (Nimotop ®) after dilution with 0.9% sodium chloride

| Time(h) | Sample name | Content (%) | Appearance |
|---|---|---|---|
| 0 | Nimotop ® | 99.49 | − |
| | Nimodipine for Injection | 99.74 | − |
| 3 | Nimotop ® | 34.65 | + |
| | Nimodipine for Injection | 99.32 | − |

TABLE 26-continued

| Changes in the content of nimodipine for injection and nimodipine injection (Nimotop ®) after dilution with 0.9% sodium chloride | | | |
|---|---|---|---|
| Time(h) | Sample name | Content (%) | Appearance |
| 6 | Nimotop ® | 31.86 | + |
| | Nimodipine for Injection | 98.56 | – |
| 9 | Nimotop ® | 6.23 | + |
| | Nimodipine for Injection | 99.13 | – |
| 12 | Nimotop ® | 3.52 | + |
| | Nimodipine for Injection | 99.81 | – |
| 24 | Nimotop ® | 2.49 | + |
| | Nimodipine for Injection | 99.93 | – |

Note:
"–" indicates that the drug is not precipitated, and "+" indicates that the drug is precipitated.

TABLE 27

| Changes in the content of nimodipine for injection and nimodipine injection (Nimotop ®) after dilution with 5% dextrose | | | |
|---|---|---|---|
| Time(h) | Sample name | Content (%) | Appearance |
| 0 | Nimotop ® | 99.62 | – |
| | Nimodipine for Injection | 100.41 | – |

TABLE 27-continued

| Changes in the content of nimodipine for injection and nimodipine injection (Nimotop ®) after dilution with 5% dextrose | | | |
|---|---|---|---|
| Time(h) | Sample name | Content (%) | Appearance |
| 3 | Nimotop ® | 41.54 | + |
| | Nimodipine for Injection | 99.84 | – |
| 6 | Nimotop ® | 16.35 | + |
| | Nimodipine for Injection | 99.23 | – |
| 9 | Nimotop ® | 8.92 | + |
| | Nimodipine for Injection | 98.79 | – |
| 12 | Nimotop ® | 7.64 | + |
| | Nimodipine for Injection | 99.42 | – |
| 24 | Nimotop ® | 6.51 | + |
| | Nimodipine for Injection | 99.01 | – |

Note:
"–" indicates that the drug is not precipitated, and "+" indicates that the drug is precipitated.

Nimotop® was diluted with 0.9% sodium chloride or 5% dextrose, and a large amount of the drug was precipitated at 3 h. The content of the drug decreased significantly at 24 h, and the dilution stability was extremely poor. Nimodipine for injection of the present disclosure diluted with 0.9% sodium chloride or 5% dextrose did not significantly change the content at 24 h, the appearance was clear, and the dilution stability was good. The above results show that, compared with Nimotop®, the dilution stability of Nimodipine for injection of the present disclosure is significantly improved, with obvious advantages.

Example 67: Stability Study of Nimodipine for Injection Under Various Conditions and Acceleration Stability Test 1. Experimental Methods The nimodipine for injection prepared in Example 48 was examined for stability under conditions of high temperature, high humidity, light exposure, and accelerated testing according to the "9001 Guiding Principles for Stability Test of Raw Materials and Preparations" in the "Pharmacopoeia of the People's Republic of China" in 2020. The changes in drug content and related substances were detected.

2. Experimental Results

TABLE 28

Stability Study Results of Nimodipine for Injection

| | | | | Related substances (%) | | | | |
|---|---|---|---|---|---|---|---|---|
| Research project | time | character | Content (%) | impurity B | impurity C | impurity I | other impurities | Total impurities |
| initial value | | Yellowish loose mass | 99.20 | 0.17 | 0.26 | not detected | 0.07 | 0.50 |
| high-temperature test | one month | Yellowish loose mass | 99.52 | 0.18 | 0.27 | not detected | 0.08 | 0.53 |
| High-humidity test | ten-day | Yellowish loose mass | 99.43 | 0.16 | 0.27 | not detected | 0.08 | 0.51 |
| illumination experiment | ten-day | Yellowish loose mass | 96.59 | 0.17 | 0.28 | 0.07 | 0.09 | 0.61 |
| acceleration test | Six months | Yellowish loose mass | 99.63 | 0.18 | 0.26 | not detected | 0.08 | 0.52 |

3. Result Analysis

The content and related substances of nimodipine for injection showed minimal changes under conditions of high temperature, high humidity, and accelerated testing. However, after light exposure for 10 days, the content decreased to 96.59%, with an increase in related substances of 0.11%. This finding indicates that nimodipine is less stable and easy to decompose under light conditions, even after being encapsulated by cyclodextrin, nimodipine still degrades under light conditions, indicating that nimodipine for injection should be stored away from light. These results demonstrate that nimodipine for injection has good stability and meets quality requirements.

Example 68: Vascular Irritation Study of Nimodipine for Injection

1. Experimental Methods

Six rabbits (weighing 1.8-2.0 kg) were randomly divided into two groups. The nimodipine for injection prepared in Example 48 redissolved with water for injection and the commercial Nimotop® were respectively diluted with 0.9% sodium chloride solution to a clinical concentration of 0.04 mg/mL. The solution was administered through the right ear margin vein of rabbits at a dose of 0.4 mg/kg at a speed of 1 mL/min. The left ear margin vein received an equal volume of 0.9% sodium chloride solution as a control. During the administration of each day, the behaviour of the animal and the change of the injection site were visually observed. Euthanasia was performed 24 to 48 h after the last administration, and vein tissue of the ear margin at a distance of about 0.5 to 3.0 cm from the injection site on both sides were taken to be fixed in a 10% paraformaldehyde solution, dehydrated using an ethanol gradient, embedded in paraffin, stained with a hematoxylin-eosin solution, and pathological changes were evaluated.

2. Experimental Results

Figure 5:
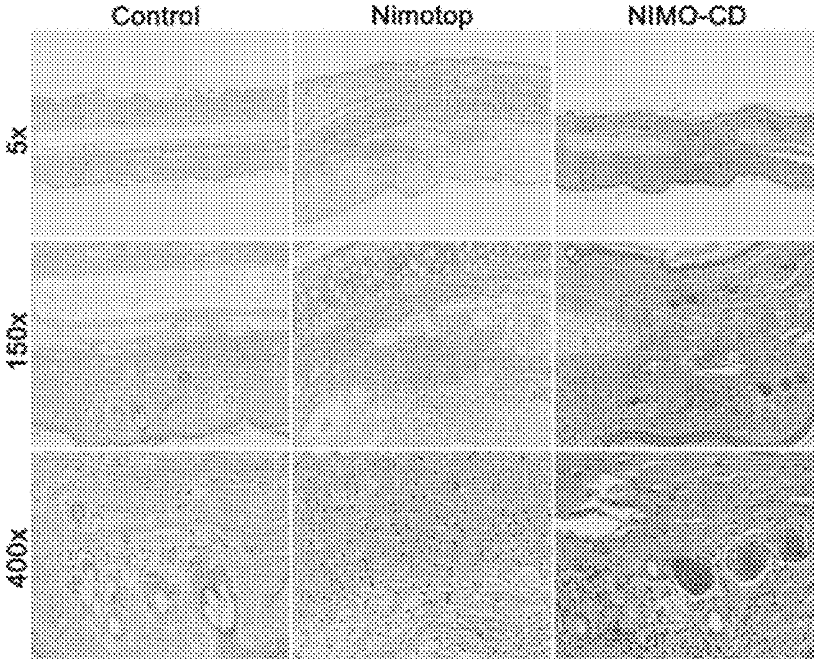
FIG. 5 Pathological slides of vascular irritation with nimodipine for injection.

The pathological results of vascular irritation in the rabbit ear sections are shown in FIG. 5.

Nimotop® caused significant collagen swelling, red blood cell leakage, and pinpoint hemorrhages, with extensive inflammatory cell infiltration, indicating a strong inflammatory response after administration of Nimotop®. During administration, rabbits exhibited severe pain and struggled violently, likely because the high ethanol concentration caused strong vascular irritation.

In contrast, the nimodipine for injection and 0.9% sodium chloride injection resulted in a complete epithelial structure, with no special changes in sebaceous or sweat glands, and a normal cartilage morphology in the central area. No obvious pathological changes and injuries were found, and the rabbits had no obvious discomfort during the administration. Compared with 0.9% sodium chloride injection group, nimodipine for injection had only a small amount of inflammatory cells infiltration, and no other abnormalities were found.

These results indicate that the degree of vascular irritation caused by nimodipine for injection is significantly lower than that caused by Nimotop®, demonstrating improved safety.

Example 69: Hemolytic Study of Nimodipine for Injection

1. Experimental Methods

The nimodipine for injection prepared in Example 48 redissolved with water for injection were respectively diluted with 0.9% sodium chloride solution to a clinical concentration of 0.04 mg/mL. The hemolysis test was conducted using clean glass tubes numbered 1 to 8, with different concentrations of NIMO-CD in tubes 1 to 5, a negative control in tube 6, a positive control in tube 7, and a Nimotop® in tube 8. As shown in the following table, 2% red blood cell suspension, 0.9% sodium chloride injection, distilled water, and pharmaceutical solution were added successively, and after mixing, the samples were immediately placed in a 37±0.5° C. water bath for warming, and the hemolysis of each tube was observed and recorded. First, it was recorded every 15 minutes, and after 1 hour, it was observed every 1 hour for 3 hours.

TABLE 29

Design of the hemolysis experiment

| Test tube number | 1 | 2 | 3 | 4 | 5 | 6 | 7 | 8 |
|---|---|---|---|---|---|---|---|---|
| 2% Red Blood Cell Suspension (mL) | 2.5 | 2.5 | 2.5 | 2.5 | 2.5 | 2.5 | 2.5 | 2.5 |
| 0.9% Sodium Chloride Injection (mL) | 2.0 | 2.1 | 2.2 | 2.3 | 2.4 | 2.5 | | 2.0 |
| Distilled Water (mL) | | | | | | | 2.5 | |
| NIMO-CD (mL) | 0.5 | 0.4 | 0.3 | 0.2 | 0.1 | | | |
| Nimotop ® (mL) | | | | | | | | 0.5 |

2. Experimental Results

Figure 6:
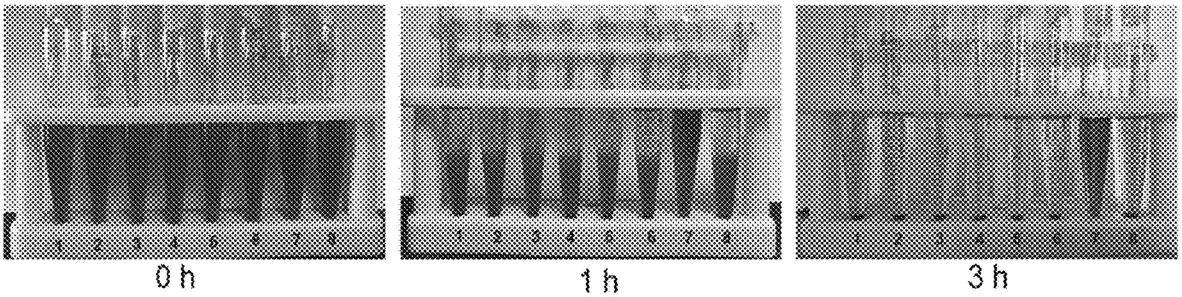
FIG. 6 Diagram of the hemolytic effect of nimodipine for injection.

As shown in FIG. 6, NIMO-CD (Nos. 1-5) red blood cells were deposited at the bottom of the test tube, and the supernatant was colorless, clear, and uniformly dispersed after shaking, indicating that NIMO-CD did not cause hemolysis or red blood cell aggregation. The above results show that nimodipine for injection has no hemolysis and can be used by injection.

Example 70: Pharmacodynamics of Nimodipine for Injection

1. Experimental Methods 1.1 Grouping and Administration of Experimental Animals

Thirty-two male SD rats were randomly divided into 4 groups: the Sham group, Model control group, Nimotop® group (Nimotop group) and Nimodipine for injection group (NIMO-CD group, example 48). Nimodipine for injection prepared in example 48 was redissolved with water for injection and diluted to 0.2 mg/mL by 0.9% sodium chloride injection. The Nimotop® group and the NIMO-CD group were treated via the caudal vein at a dose of 1 mg/kg once a day from the day of modeling to 72 h after surgery and then immediately after surgery.

1.2 Establishment of a Cerebral Hemorrhage Model

After 1-4% isoflurane anesthesia in the Model group, Nimotop group and NIMO-CD group, a brain stereotaxometer was used to detect the left striatal region (with the fontanel as the center, posterior 2.0 mm, right 2.0 mm, depth 4.0 mm) needle insertion for 2 min, 2 mg/mL collagenase solution for 2 μL at a rate of 1 L/5 min, needle insertion for 3 min and slow removal to establish a cerebral hemorrhage model. After surgery, the wound was sutured and disinfected with iodophor. An intramuscular injection of 40 mg/kg gentamicin in the hind limb was given to prevent infection, and an intramuscular injection of 10 mg/kg Tilidine was given twice daily to relieve pain. The animal experiments in the Sham group were performed as above, and the same volume of PBS solution was used instead of collagenase injection.

1.3 Detection Indicators 1.3.1 Behavioral Evaluation

The behavior of the animals was observed before the operation and at 24, 48 and 72 hours after the establishment of the intracerebral hemorrhage model. The modified neurological severity score (mNSS) was used to evaluate the motor, sensory, balance and reflexes of the experimental animals. Sensorimotor disorders were measured by the corner test (CT). The rat was placed into a 30-degree angle formed by two boards, which were turned around, and the number of turns to the right side of the rat was recorded. The angle was tested 10 times, and the CT score formula was calculated as follows.

$$CT\ \text{scores} = \frac{\text{The number of times turn to the healthy side(This test is on the right side)}}{\text{Total number of turns}} * 100\%$$

1.3.2 Area of Cerebral Hemorrhage Injury

At the end of the experiment, all the experimental animals were anesthetized and euthanized via intraperitoneal injection of 25-50 mg/kg Zoletil. The brain was removed and fixed in 4% paraformaldehyde solution for 24 h. The brain was placed in a brain mold and cut into 6 pieces from front to back in a coronal fashion with the needle insertion position at the center. The 6 brain slices were arranged in order, and a ruler was attached to the slices for imaging by a digital camera. The image analysis software ImageJ (version 1.4.3.67) was used to calculate the proportion of the hematoma area in each film and compare the differences in the total hematoma area between the groups. If the animal died during the experiment, the brain was removed immediately and processed as described above.

1.3.3 Histopathological Evaluation

The brain sections of the rats were fixed with 4% paraformaldehyde solution, embedded in paraffin and subjected to HE staining, and pathological changes were observed via optical microscopy. The degree of cerebral edema, inflammatory immersion and neuronal injury in the sections was evaluated according to the histopathological scoring criteria, as shown in Table 30.

TABLE 30

Histopathological scoring criteria

| Score | Degree of cerebral edema | inflammatory infiltration | neuron damage |
|---|---|---|---|
| 0 | No edema | Without inflammation | No neuronal damage |
| 1 | Mild edema | Mild, occasionally inflammatory infiltration | Mild and occasional structural damage of neurons was observed |
| 2 | Moderate edema | The area of inflammatory infiltration increased, and multiple sites dispersed | Moderate neuronal damage |
| 3 | Moderate to severe edema | The area and incidence of increased inflammatory infiltration | Moderate-severe neuronal damage that continues to develop |
| 4 | Severe edema | Inflammatory infiltration seen everywhere | Extensive neuronal damage seen everywhere |

2. Experimental Results 2.1 Behavioral Evaluation

Figure 7A:
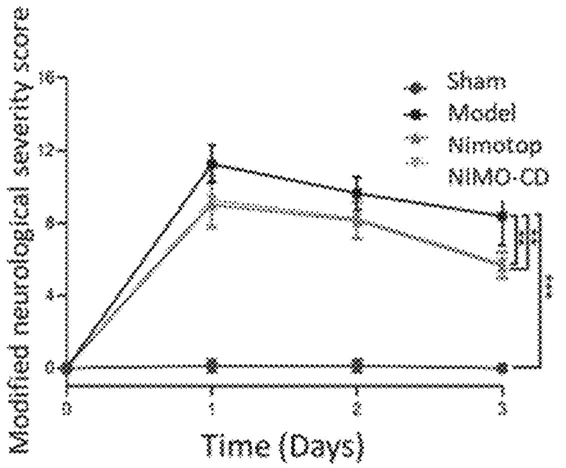
FIG. 7A-7E Pharmacodynamic evaluation of nimodipine for injection.

The results of the behavioral evaluation of the mNSS are shown in Table 31 and FIG. 7A. The international standard definition of the mNSS is as follows: normal SD rats, 0 points; mild injuries, between 1-6 points; moderate injuries, between 7-12 points; and severe injuries, between 13-18 points. The mNSS score of the Model group was the highest on the first day, and neurological function damage was the most severe. On the second and third days, the scores gradually decreased, and neurological function gradually recovered, but all scores were greater than 7 points, indicating moderate damage. The neurological function scores of the Nimotop group and the NIMO-CD group also decreased with time, the scores at two days after treatment were greater than 7 points, indicating moderate injury, and the scores at three days were lower than 7 points, indicating mild injury. Compared with those of the model group, the mNSSs of the experimental animals in the Nimotop group and the NiMO-CD group were significantly lower.

TABLE 31 mNSS rating scale (mean ± SD, n = 8)

| Group | mNSS scores Day 0 | Day 1 | Day 2 | Day 3 |
|---|---|---|---|---|
| Sham group | 0.00 | 0.13 ± 0.35 | 0.13 ± 0.35 | 0.00*** |
| Model group | 0.00 | 11.25 ± 1.04 | 9.63 ± 0.92 | 8.37 ± 1.60 |
| Nimotop group | 0.00 | 9.00 ± 1.31 | 8.13 ± 0.99 | 5.63 ± 0.74** |
| Nimo-CD group | 0.00 | 9.25 ± 1.39 | 8.25 ± 1.04 | 5.75 ± 0.71** |

Note:
Compared with the Model group,
*P < 0.05,
**P < 0.01,
***P < 0.001.

Figure 7B:
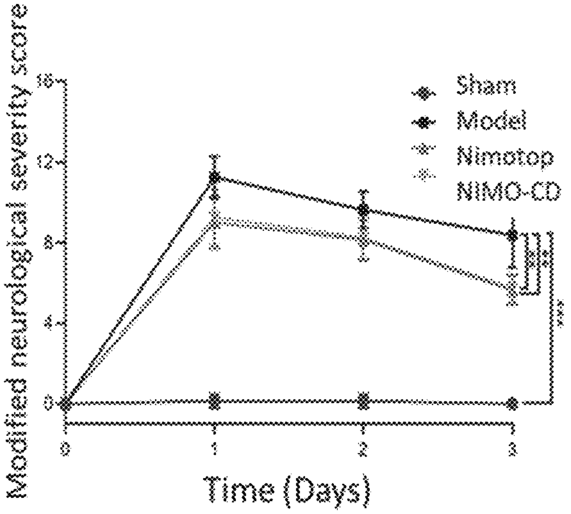

The CT score results are shown in Table 32 and FIG. 7B. The CT scores decreased with time, and the hemiplegia of the experimental animals in each group gradually improved. The final CT scores of the Sham group and Model group were 48.75% and 65.00%, respectively, and the final CT scores of the NIMO-CD group and Nimotop group were 58.75% and 60.00%, respectively. Compared with those of the model group, the CT scores of the experimental animals in the Nimotop group and the NIMOCD group were lower.

TABLE 32

| CT score table (mean ± SD, n = 8) | | | | |
|---|---|---|---|---|
| | CT grade (%) | | | |
| Group | Day 0 | Day 1 | Day 2 | Day 3 |
| Sham group | 51.25 ± 6.41 | 50.00 ± 5.35 | 48.75 ± 3.54 | 48.75 ± 3.54*** |
| Model group | 51.25 ± 6.41 | 76.25 ± 9.16 | 70.00 ± 7.56 | 65.00 ± 7.56 |
| Nimotop group | 52.50 ± 4.63 | 72.50 ± 7.07 | 67.50 ± 7.07 | 60.00 ± 7.56 |
| Nimo-CD group | 52.50 ± 4.63 | 72.50 ± 7.07 | 65.00 ± 9.26 | 58.75 ± 6.41 |

Note: Compared with the Model group, *P<0.05,  P<0.01, * P<0.001.

The results of the behavioral evaluation revealed that nimodipine for injection significantly improved the neurobehavioral dysfunction induced by brain injury in rats with cerebral hemorrhage, and there was no significant difference between the nimodipine for injection group and the Nimotop® group (P>0.05).

2.2 Area of Cerebral Hemorrhage Injury

Figure 7C:
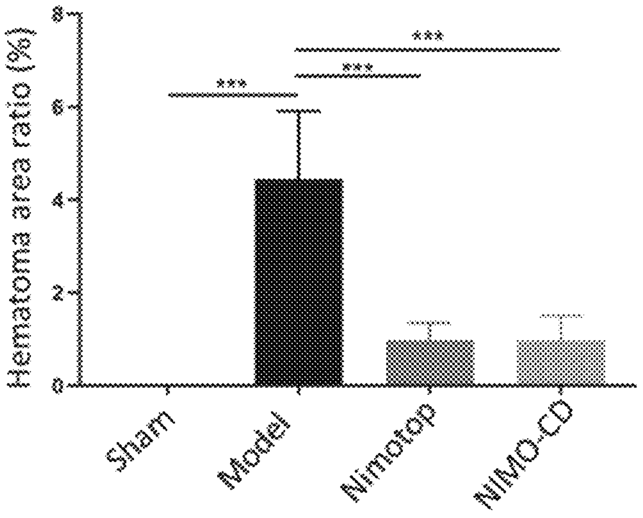

The brain tissues of the test animals were collected, and the differences in the total hematoma area among all the groups were compared, as shown in Table 33 and FIG. 7C. There were no hematomas in the sham group; the total hematoma area accounted for 4.45% of the total hematoma area in the model group and 0.98% of the total hematoma area in both the Nimotop and NIMO-CD groups. Compared with that in the Model group, the proportion of the total hematoma area in the Nimotop group and the NiMO-CD group was significantly lower. The experimental results revealed that nimodipine for injection could significantly reduce the hematoma caused by cerebral hemorrhage in rats and significantly improve cerebral hemorrhage injury, and there was no significant difference between nimodipine for injection and Nimotop® (P>0.05).

TABLE 33

| Intracerebral hemorrhage injury area (mean ± SD, n = 8) | |
|---|---|
| Group | Proportion of total hematoma area (%) |
| Sham group | 0.00*** |
| Model group | 4.45 ± 1.46 |
| Nimotop group | 0.98 ± 0.38*** |
| NIMO - CD group | 0.98 ± 0.54*** |

Note:
Compared with the Model group,
*P < 0.05,
**P < 0.01,
***P < 0.001.

2.3 Histopathological Evaluation

Figure 7D:
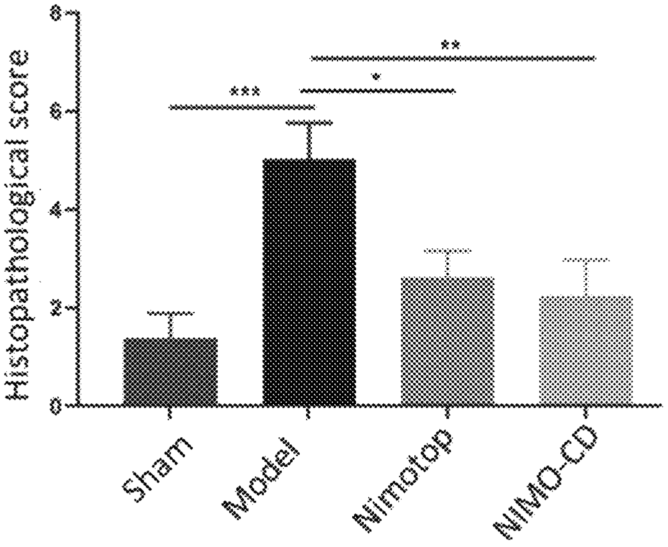
Figure 7E:
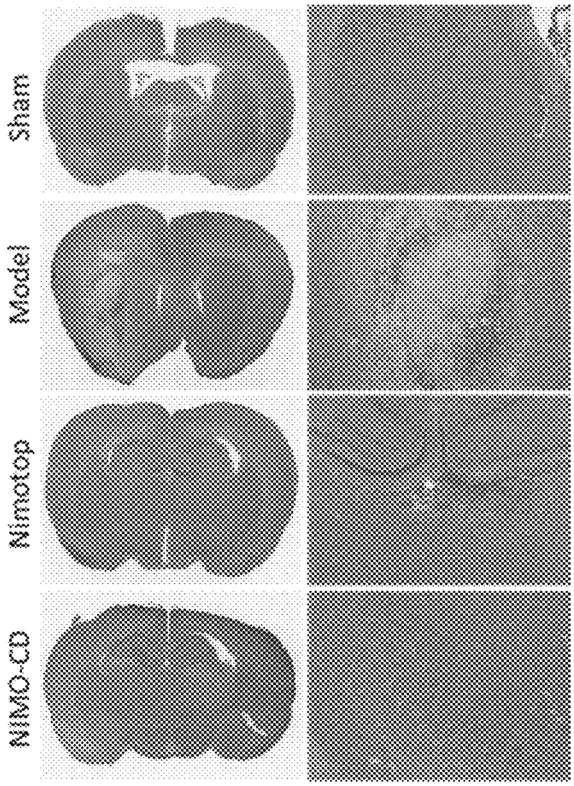

The brain tissue sections were observed and analyzed microscopically. The pathological sections are shown in FIG. 7E. The degree of cerebral edema, degree of inflammation and degree of neuronal damage were comprehensively scored in the pathological sections. The scoring results are shown in Table 34 and FIG. 7D. The histopathological evaluation scores of the sham group and model group were 1.38 and 5.00, respectively. The histopathological evaluation scores of the Nimotop group and the NIMO-CD group were 2.63 and 2.25, respectively. Compared with that of the model group, the total histopathological evaluation score of the experimental animals in the NIMO-CD group was lower. Histopathological results revealed that nimodipine for injection could significantly improve the degree of cerebral edema, inflammation and neuronal injury, and there was no significant difference between nimodipine for injection and Nimotop® (P>0.05).

TABLE 34

| Histopathological data (mean ± SD, n = 8) | | | | |
|---|---|---|---|---|
| | Histopathological evaluation | | | |
| Group | Degree of cerebral edema | Degree of inflammation | neuron damage | total points |
| Sham group | 0.13 ± 0.33 | 0.63 ± 0.48 | 0.63 ± 0.48 | 1.38 ± 0.48*** |
| Model group | 1.75 ± 0.43 | 1.25 ± 0.43 | 2.00 ± 0.00 | 5.00 ± 0.71 |
| Nimotop group | 0.75 ± 0.43 | 1.13 ± 0.33 | 0.75 ± 0.43 | 2.63 ± 0.48** |
| Nimo-CD group | 0.63 ± 0.48 | 0.75 ± 0.66 | 0.88 ± 0.33 | 2.25 ± 0.66* |

Note:
Compared with the Model group,
*P < 0.05,
**P < 0.01,
***P < 0.001.

In summary, nimodipine for injection has a significant therapeutic effect on the prognosis of cerebral hemorrhage, greatly improving the degree of nerve function injury, cerebral hematoma, cerebral edema, inflammation and neuronal injury caused by cerebral hemorrhage, and the therapeutic effect is basically the same as that of Nimotop®.

Example 71: Pharmacokinetic Study of Nimodipine for Injection

1. Experimental Methods 1.1 Experimental Animal Grouping and Administration

Sixteen male SD rats were randomly divided into two groups, with 8 rats in each group. The rats were fasted for 12 hours before the experiment but had free access to water. Nimodipine for injection (NIMO-CD) prepared in Example 48 was redissolved with water for injection and diluted with 0.9% sodium chloride injection to a concentration of 0.2 mg/mL. Each rat was injected with 1.6 mg/kg Nimotop or NIMO-CD via the tail vein. Blood samples (0.5 mL) were collected from the orbital plexus at 5, 15, 30, 45, 60, 120, 240, 360, and 480 minutes after administration. The samples were centrifuged at 4000 rpm for 5 minutes, and 300 μL of the supernatant was stored at −80° C.

1.2 Plasma Sample Processing Method

The frozen plasma samples were heated to room temperature and centrifuged at 4000 rpm for 5 minutes, 200 μL of plasma was collected, placed in a 2.0 mL EP tube, 40 μL of 5 μg/mL nicardipine internal standard solution was added, and the mixture was vortexed for 5 minutes. Then, 100 μL of 1 mol/L NaOH was added, and 1.5 mL of anhydrous ether: n-hexane (1:1) extraction mixture was added. The mixture was vortexed for 5 minutes, sonicated for 5 minutes, and centrifuged at 10000 rpm for 10 minutes. All the supernatant was transferred to a 1.5 mL EP tube, evaporated at 45° C. until dry, redissolved with 100 μL of the mobile phase, vortexed for 5 minutes, centrifuged at 10000 rpm for 10 minutes, and injected into an HPLC system for determination.

1.3 Chromatographic Conditions

Column: Zorbax SB C18 column (250 mm×4.6 mm, 5 μm)

Mobile phase: acetonitrile:water (60:40, v/v)

Flow rate: 1.0 mL/min

Detection wavelength: 358 nm

Column temperature: 30° C.

Injection volume: 20 μL

2. Experimental Results

Figure 8:
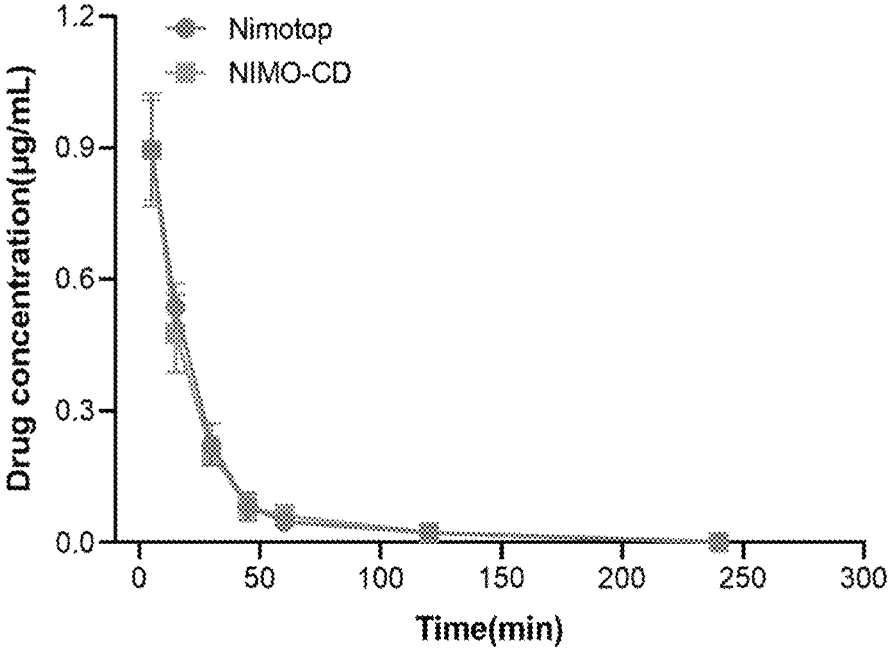
FIG. 8 Blood concentration-time profile of nimodipine for injection.

The blood concentration-time curves of the SD rats after tail vein injection of Nimotop or NIMO-CD are shown in FIG. 8. The pharmacokinetic elimination curves of NIMO-CD and Nimotop in SD rats were almost identical after intravenous administration. Following the administration of NIMO-CD and Nimotop injection, NIMO is rapidly eliminated from the body within a short period, and the drug is undetectable in plasma by HPLC 240 minutes after administration.

The main pharmacokinetic parameters of NIMO-CD and Nimotop injection are shown in Table 35. The results indicate that the pharmacokinetic parameters of NIMO-CD and Nimotop injection are basically consistent, including the area under the blood concentration-time curve (AUC), mean residence time (MRT), half-life (t½), clearance rate (CL), and maximum blood concentration (Cmax), with no statistically significant differences between the groups (P>0.05). These results demonstrate that the pharmacokinetic properties of nimodipine for injection and Nimotop® are essentially consistent following tail vein injection in SD rats.

TABLE 35

Major Pharmacokinetic Parameters of NIMO-CD and Nimotop ® (Mean ± SD, n = 8)

| Parameters | Unit | NIMO-CD | Nimotop |
|---|---|---|---|
| AUC(0-1) | mg/L · min | 22.792 ± 1.630 | 23.740 ± 2.431 |
| AUC(0-∞) | mg/L · min | 23.549 ± 3.369 | 23.773 ± 2.447 |
| MRT (0-t) | min | 21.094 ± 1.790 | 20.296 ± 1.196 |
| MRT (0-∞) | min | 26.431 ± 4.139 | 22.470 ± 1.257 |
| t1/2 | min | 17.028 ± 2.329 | 16.203 ± 1.633 |
| CL | L/min/kg | 0.068 ± 0.006 | 0.068 ± 0.008 |
| Cmax | mg/L | 0.896 ± 0.104 | 0.637 ± 0.400 |

The above has specifically described the preferred embodiments of the present disclosure, but the present disclosure is not limited to these embodiments. Those skilled in the art can make various equivalent modifications or substitutions without departing from the spirit of the present disclosure, and these equivalent modifications or substitutions are included within the scope defined by the claims of the present disclosure.

What is claimed is:

1. A safe and stable nimodipine formulation for injection comprising sulfobutyl ether-β-cyclodextrin and nimodipine, wherein the mass ratio of sulfobutyl ether-β-cyclodextrin to nimodipine is 350:1 to 700:1.

2. The nimodipine for injection according to claim 1, wherein the content of nimodipine is 0.01-0.14% g/mL, and the content of sulfobutyl ether-β-cyclodextrin is 10-50% g/mL.

3. The safe and stable nimodipine formulation for injection according to claim 1, wherein the mass ratio of sulfobutyl ether-β-cyclodextrin to nimodipine is 400:1 to 600:1, the content of nimodipine is 0.02-0.10% g/mL, and the content of sulfobutyl ether-β-cyclodextrin is 10-40% g/mL.

4. The safe and stable nimodipine formulation for injection according to claim 1, wherein the mass ratio of sulfobutyl ether-β-cyclodextrin to nimodipine is 450:1 to 550:1, the content of nimodipine is 0.04-0.06% g/mL, and the content of sulfobutyl ether-β-cyclodextrin is 20-30% g/mL.

5. A safe and stable nimodipine formulation for injection comprising sulfobutyl ether-β-cyclodextrin and nimodipine, wherein the mass ratio of sulfobutyl ether-β-cyclodextrin to nimodipine is 350:1 to 700:1; and the nimodipine formulation for injection comprises:

| | |
|---|---|
| Nimodipine | 0.01-0.20% g/mL |
| Sulfobutyl ether-β-cyclodextrin | 10-50% g/mL |
| Ethanol | 0-5% mL/mL |
| Water for injection | Balance. |

6. The safe and stable nimodipine formulation for injection according to claim 5, wherein the nimodipine formulation for injection comprises:

| | |
|---|---|
| Nimodipine | 0.01-0.14% g/mL |
| Sulfobutyl ether-β-cyclodextrin | 10-50% g/mL |
| Ethanol | 0-3.5% mL/mL |
| Water for injection | Balance. |

7. A preparation method for the safe and stable nimodipine formulation for injection as described in claim 5, wherein the preparation method comprises the following steps:

(a) weighing the prescribed amount of sulfobutyl ether-β-cyclodextrin, adding an appropriate amount of water for injection, and stirring at a certain temperature to dissolve to obtain a sulfobutyl ether-β-cyclodextrin aqueous solution;

(b) weighing the prescribed amount of nimodipine and adding the prescribed amount of ethanol to dissolve to obtain a nimodipine ethanol solution;

(c) adding the solution of step (b) or nimodipine powder to the solution of step (a) under a certain stirring temperature and speed, stirring for a certain period, adding water for injection to the full amount, sterilely filtering with a 0.22 μm microporous filter membrane, filling, freeze-drying, and packaging to obtain the safe and stable nimodipine for injection.

8. The preparation method according to claim 7, wherein the stirring temperature in steps (a) and (c) is 20-100° C.

9. The preparation method according to claim 7, wherein the stirring time in step (c) is 10-300 minutes.

10. The preparation method according to claim 7, wherein the stirring speed in step (c) is 0.5-10.0 m/s.

11. The safe and stable nimodipine formulation for injection according to claim 1, wherein the nimodipine formulation has a dilution stability time of more than 24 h.

12. The safe and stable nimodipine formulation for injection according to claim 5, wherein the nimodipine formulation has a dilution stability time of more than 24 h.

* * * * *